US006774127B2

(12) United States Patent
Adams et al.

(10) Patent No.: US 6,774,127 B2
(45) Date of Patent: Aug. 10, 2004

(54) PYRAZOLE AND PYRAZOLINE SUBSTITUTED COMPOUNDS

(75) Inventors: Jerry L. Adams, Wayne, PA (US); Timothy Gallagher, Harleysville, PA (US); Irennegbe Kelly Osifo, Norristown, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 46 days.

(21) Appl. No.: 10/369,398

(22) Filed: Feb. 19, 2003

(65) Prior Publication Data

US 2003/0153569 A1 Aug. 14, 2003

Related U.S. Application Data

(62) Division of application No. 09/214,452, filed as application No. PCT/US98/12387 on Jun. 12, 1998, now abandoned.
(60) Provisional application No. 60/050,904, filed on Jun. 13, 1997.

(51) Int. Cl.$^7$ .................... A61K 31/53; A61K 31/5355; A61K 31/496; A61K 31/499; C07D 403/04; C07D 413/06
(52) U.S. Cl. .................. 514/242; 514/252.05; 544/238; 544/242; 544/405; 544/180; 544/111; 544/112; 544/120
(58) Field of Search ................................. 544/111, 112, 544/120, 238, 242, 405, 180; 514/242, 252.05

(56) References Cited

U.S. PATENT DOCUMENTS

| 2,833,779 A | 5/1958 | Fields et al. |
| 3,678,063 A | 7/1972 | Binon et al. |
| 3,707,475 A | 12/1972 | Lombardino ................ 260/309 |
| 3,772,441 A | 11/1973 | Lombardino ................ 424/273 |
| 3,929,807 A | 12/1975 | Fitzi .................... 260/294.8 R |
| 3,940,486 A | 2/1976 | Fitzi ............................ 424/263 |
| 4,032,526 A * | 6/1977 | Cross et al. ................. 544/371 |
| 4,058,614 A | 11/1977 | Baldwin ....................... 424/263 |
| 4,199,592 A | 4/1980 | Cherkofsky ................. 424/273 |
| 4,447,431 A | 5/1984 | Sallmann .................... 424/246 |
| 4,503,065 A | 3/1985 | Wilkerson .................. 514/396 |
| 4,565,875 A | 1/1986 | Cavender .................... 548/336 |
| 4,686,231 A | 8/1987 | Bender et al. ............... 514/333 |
| 4,822,805 A | 4/1989 | Tasasugi et al. ............ 514/341 |
| 5,389,648 A * | 2/1995 | Tsuboi et al. ............... 514/333 |
| 5,516,907 A | 5/1996 | Talley et al. |
| 5,559,137 A | 9/1996 | Adams et al. |
| 5,580,985 A | 12/1996 | Lee et al. |
| 5,593,991 A | 1/1997 | Adams et al. ........... 514/235.2 |
| 5,593,992 A | 1/1997 | Adams et al. ........... 514/235.8 |
| 5,656,644 A | 8/1997 | Adams et al. ............... 514/341 |
| 5,658,903 A | 8/1997 | Adams et al. ........... 514/235.8 |
| 5,663,334 A | 9/1997 | Adams et al. ............... 544/122 |
| 5,670,527 A | 9/1997 | Adams et al. ............... 514/341 |
| 5,686,455 A | 11/1997 | Adams et al. ............... 514/256 |
| 5,716,955 A | 2/1998 | Adams et al. ........... 514/235.8 |
| 5,716,972 A | 2/1998 | Adams et al. ............... 514/314 |
| 5,739,143 A | 4/1998 | Adams et al. ............... 514/275 |
| 5,756,499 A | 5/1998 | Adams et al. ........... 514/235.8 |
| 5,777,097 A | 7/1998 | Lee et al. ................. 536/24.31 |
| 5,783,664 A | 7/1998 | Lee et al. .................... 530/350 |
| 5,811,549 A | 9/1998 | Adams et al. ............... 544/123 |
| 5,864,036 A | 1/1999 | Adams et al. ............... 544/123 |
| 5,869,043 A | 2/1999 | McDonnell et al. ....... 424/94.1 |
| 5,869,660 A | 2/1999 | Adams et al. ............... 544/122 |
| 5,871,934 A | 2/1999 | Lee et al. ..................... 435/7.1 |
| 5,916,891 A | 6/1999 | Adams et al. ............... 514/256 |
| 5,917,043 A | 6/1999 | Sisko ......................... 544/332 |
| 5,929,076 A | 7/1999 | Adams et al. ............... 514/252 |
| 5,955,366 A | 9/1999 | Lee et al. .................... 435/471 |
| 5,969,184 A | 10/1999 | Adams et al. ............... 564/154 |
| 5,977,103 A | 11/1999 | Adams et al. ........... 514/235.2 |
| 5,998,425 A | 12/1999 | Adams et al. ............... 514/275 |
| 6,008,235 A | 12/1999 | Adams et al. ............... 514/333 |

FOREIGN PATENT DOCUMENTS

| EP | 0 477 049 A1 | 8/1991 | |
| WO | WO 92/10190 | 6/1992 | .......... A61K/31/44 |
| WO | WO 92/10498 | 6/1992 | ......... C07D/487/00 |
| WO | WO 94/19350 | 9/1994 | ......... C07D/487/04 |
| WO | WO 95/02591 | 1/1995 | ......... C07D/401/04 |
| WO | WO 95/03297 | 2/1995 | ......... C07D/401/04 |
| WO | WO 95/09851 | 4/1995 | ......... C07D/401/04 |
| WO | WO 95/13067 | 5/1995 | .......... A61K/31/44 |
| WO | WO 95/31451 | 11/1995 | ......... C07D/401/04 |
| WO | WO 96/21452 | 7/1996 | ......... A61K/31/535 |
| WO | WO 96/21654 | 7/1996 | ......... C07D/233/00 |
| WO | WO 96/40143 | 12/1996 | ......... A61K/31/505 |
| WO | WO 97/12876 | 4/1997 | ......... C07D/233/76 |
| WO | WO 97/16426 | 5/1997 | ......... C07D/207/30 |
| WO | WO 97/23479 | 7/1997 | ......... C07D/401/14 |
| WO | WO 97/25045 | 7/1997 | ......... A61K/31/505 |
| WO | WO 97/25046 | 7/1997 | ......... A61K/31/505 |
| WO | WO 97/25047 | 7/1997 | ......... A61K/31/505 |
| WO | WO 97/25048 | 7/1997 | ......... A61K/31/505 |
| WO | WO 97/32583 | 9/1997 | .......... A61K/31/44 |

(List continued on next page.)

OTHER PUBLICATIONS

97/25046
de Silva et al., Luminescence and charge transfer . . . , J. Chem. Soc., (1995), (4) pp. 685–690.
Lamartina et al., "New Imidazolylpyrazoles of potential pharmaceutical interest", Boll. Chim. Farm., 1990, 129(12), pp. 314–316.
Vartanyan et al., "The synthesis of 1–phenyl–3–methyl–5–(1–methyl–4–piperidyl) . . . ", 1987, 40(9), pp. 552–560.
Ferles et al., "Studies in the pyridine series", Collect. Czech. Chem. Commun., 1981, (46)5, pp. 1167–1172.

(List continued on next page.)

Primary Examiner—Rita Desai
(74) Attorney, Agent, or Firm—Dara L. Dinner; Stephen Venetianer; Charles M. Kinzig

(57) ABSTRACT

Novel pyridyl and pyrimidinyl substituted pyrazole and pyrazoline compounds and compositions for use in therapy.

19 Claims, No Drawings

FOREIGN PATENT DOCUMENTS

| WO | WO 97/33883 | 9/1997 | C07D/401/04 |
|---|---|---|---|
| WO | WO 97/35855 | 10/1997 | C07D/401/04 |
| WO | WO 97/35856 | 10/1997 | C07D/401/04 |
| WO | WO 97/36587 | 10/1997 | A61K/31/44 |
| WO | WO 97/47618 | 12/1997 | C07D/403/14 |
| WO | WO 98/06751 | 2/1998 | C07D/403/06 |
| WO | WO 98/07425 | 2/1998 | A61K/31/44 |
| WO | WO 98/16230 | 4/1998 | A61K/31/535 |
| WO | WO 98/22109 | 5/1998 | A61K/31/44 |
| WO | WO 98/25619 | 6/1998 | A61K/31/505 |
| WO | WO 98/28292 | 7/1998 | C07D/401/00 |
| WO | WO 98/47892 | 10/1998 | C07D/401/04 |
| WO | WO 98/52937 | 11/1998 | C07D/401/00 |
| WO | WO 98/52940 | 11/1998 | C07D/401/04 |
| WO | WO 98/52941 | 11/1998 | C07D/401/04 |
| WO | WO 98/56377 | 12/1998 | A61K/31/44 |
| WO | WO 98/57966 | 12/1998 | C07D/403/02 |
| WO | WO 99/00357 | 1/1999 | C07C/275/28 |
| WO | WO 99/01130 | 1/1999 | A61K/31/44 |
| WO | WO 99/01131 | 1/1999 | A61K/31/445 |
| WO | WO 99/01136 | 1/1999 | A61K/31/53 |
| WO | WO 99/01452 | 1/1999 | C07D/403/04 |
| WO | WO 99/17776 | 4/1999 | A61K/31/505 |
| WO | WO 99/18942 | 4/1999 | A61K/31/00 |
| WO | WO 99/32121 | 7/1999 | A61K/31/505 |
| WO | WO 99/57101 | 11/1999 | C07D/231/38 |
| WO | WO 99/58502 | 11/1999 | C07D/213/56 |
| WO | WO 99/58523 | 11/1999 | |
| WO | WO 99/61437 | 12/1999 | C07D/401/04 |
| WO | WO 99/61440 | 12/1999 | C07D/403/14 |
| WO | WO 99/64400 | 12/1999 | C07D/217/24 |
| WO | WO 00/12074 | 3/2000 | A61K/31/00 |
| WO | WO 00/31065 | 6/2000 | C07D/401/04 |
| WO | 03/000682 | * 1/2003 | |
| WO | 03/011837 | * 2/2003 | |

OTHER PUBLICATIONS

Fulmer et al., "An improved synthesis of 3,5–disubstittued isoxazoels . . . ", J. Heterocycl. Chem., 1980, 17(4), pp. 799–800.

Jurkowski–Kowalczyk, "Condensation of aryl pridyl . . . ", Rocz. Chem., 1977, 51(6), pp. 1191–1199.

Bradlerova et al., ".alpha., .beta.—Unsaturated ketones derived from acetylpyridines . . . ", Chem. Zvesti, 1975, 29(6), pp. 795–802.

Szucs et al., ".alpha., .beta.–Unsaturated ketones derived from acetylpyridines . . . ", Chem. Zvesti, 1972, 26(4), pp. 354–359.

Szucs et al., ".alpha., .beta.–Unsaturated ketones derived from acetylpyridines . . . ", Acta fac. Pharm. Univ. Comenianae, 1977, 30, pp. 127–146.

Mikailu et al., "Reaction of acenaphthene phosphorus ylides . . . ", Zh. Obshch. Khim, 1986, 56(7), pp. 1513–1517.

Becker et al., J. Immunol., 147, p. 4307 (1991).

Colotta et al., J. Immunol., 132(2), p. 936 (1984).

Dinarello et al., Rev.Infect.Disease, 6, p. 51 (1984).

Dinarello, J.Clin.Immun., 5(5), p. 287–297 (1985).

Kawasaki et al., J. Bio. Chem., 272(30), pp. 18518–18521.

Poli et al., Proc.Nat'l Acad.Sci., 87, p. 782–784 (1990).

Simon et al., J. Immunol. Methods, 84, p. 85 (1985).

Szucs et al., Acta Fac. Pharm. Univ. Comenianas, 30, pp. 127–146 (1977) English Translation Enclosed.

Boehm et al., "1–Substituted 4–Aryl–5–pyridinylimidazoles: A New Class of Cytokine Suppressive Drugs with Low 5–Lipoxygenase and Cyclooxygenase Inhibitory Potency", J. Med Chem, 1996, 39, pp. 3929–3937.

Wilson et al., "The structural basis of rthe specificity of pyridinylimidazole inhibitors of p38 MAP kinase", Chemistry & Biology, 1997, vol. 4 No 6, pp. 423–431.

Gallagher et al., "Regulation of Stress–Induced Cytokine Production by Pyridinylimidazoles: Inhibition of CSBP Kinase", Bioorganic & Medicinal Chemistyr, 1997, vol. 5 No 1, pp. 49–64.

* cited by examiner

US 6,774,127 B2

PYRAZOLE AND PYRAZOLINE SUBSTITUTED COMPOUNDS

This application is a divisional of U.S. Ser. No. 09/214,452, filed Dec. 13, 1999 now abandoned which is the §317 national stage entry of PCT/US98/12387, filed Jun. 12, 1998 which claims the benefit of priority from U.S. S No. 60/050,904, filed Jun. 13, 1997.

FIELD OF THE INVENTION

This invention relates to a novel group of pyrazole containing compounds, processes for the preparation thereof, the use thereof in treating cytokine mediated diseases and pharmaceutical compositions for use in such therapy.

BACKGROUND OF THE INVENTION

Intracellular signal transduction is the means by which cells respond to extracellular stimuli. Regardless of the nature of the cell surface receptor (e. g. protein tyrosine kinase or seven-transmembrane G-protein coupled), protein kinases and phosphatases along with phopholipases are the essential machinery by which the signal is further transmitted within the cell [Marshall, J. C. *Cell*, 80, 179–278 (1995)]. Protein kinases can be categorized into five classes with the two major classes being, tyrosine kinases and serine/threonine kinases depending upon whether the enzyme phosphorylates its substrate(s) on specific tyrosine(s) or serine/threonine(s) residues [Hunter, T., *Methods in Enzymology* (*Protein Kinase Classification*) p. 3, Hunter, T.; Sefton, B. M.; eds. vol. 200, Academic Press; San Diego, 1991].

For most biological responses, multiple intracellular kinases are involved and an individual kinase can be involved in more than one signaling event. These kinases are often cytosolic and can translocate to the nucleus or the ribosomes where they can affect transcriptional and translational events, respectively. The involvement of kinases in transcriptional control is presently much better understood than their effect on translation as illustrated by the studies on growth factor induced signal transduction involving MAP/ERK kinase [Marshall, C. J. *Cell*, 80, 179 (1995); Herskowitz, I. *Cell*, 80, 187 (1995); Hunter, T. *Cell*, 80, 225 (1995); Seger, R., and Krebs, E. G. *FASEB J.*, 726–735 (1995)].

While many signaling pathways are part of cell homeostasis, numerous cytokines (c.g., IL-1 and TNF) and certain other mediators of inflammation (e.g., COX-2, and iNOS) are produced only as a response to stress signals such as bacterial lippopolysaccharide (LPS). The first indications suggesting that the signal transduction pathway leading to LPS-induced cytokine biosynthesis involved protein kinases came from studies of Weinstein [Weinstein, et al., *J. Immunol.* 151, 3829(1993)] but the specific protein kinases involved were not identified. Working from a similar perspective, Han [Han, et al., *Science* 265, 808(1994)] identified murine p38 as a kinase which is tyrosine phosphorylated in response to LPS. Definitive proof of the involvement of the p38 kinase in LPS-stimulated signal transduction pathway leading to the initiation of proinflamnmatory cytokine biosynthesis was provided by the independent discovery of p38 kinase by Lee [Lee, et al., *Nature*, 372, 739(1994)] as the molecular target for a novel class of anti-inflammatory agents. The discovery of p38 (termed by Lee as CSBP 1 and 2) provided a mechanism of action of a class of anti-inflammatory compounds for which SK&F 86002 was the prototypic example. These compounds inhibited IL-1 and TNF synthesis in human monocytes at concentrations in the low $\mu$M range [Lee, et al., *Int. J. Immunopharmac.* 10(7), 835(1988)] and exhibited activity in animal models which are refractory to cyclooxygenase inhibitors [Lee, et al., *Annals N. Y. Acad. Sci.*, 696, 149 (1993)].

It is now firmly established that CSBP/p38 is a one of several kinases involved in a stress-response signal transduction pathway which is parallel to and largely independent of the analogous mitogen-activated protein kinase (MAP) kinase cascade (FIG. 1). Stress signals, including LPS, pro-inflammatory cytokines, oxidants, UV light and osmotic stress, activate kinases upstream from CSBP/p38 which in turn phosphorylate CSBP/p38 at threonine 180 and tyrosine 182 resulting in CSBP/p38 activation. MAPKAP kinase-2 and MAPKAP kinase-3 have been identified as downstream substrates of CSBP/p38 which in turn phosphorylate heat shock protein Hsp 27 (FIG. 2). It is not yet known whether MAPKAP-2, MAPKAP-3, Mnk1 or Mnk2 are involved in cytokine biosynthesis or alternatively that inhibitors of CSBP/p38 kinase might regulate cytokine biosynthesis by blocking a yet unidentified substrate downstream from CSBP/p38 [Cohen, P. *Trends Cell Biol.*, 353–361(1997)].

What is known, however, is that in addition to inhibiting IL-1 and TNF, CSBP/p38 kinase inhibitors (SK&F 86002 and SB 203580) also decrease the synthesis of a wide variety of pro-inflammatory proteins including, IL-6, IL-8, GM-CSF and COX-2. Inhibitors of CSBP/p38 kinase have also been shown to suppress the TNF-induced expression of VCAM-1 on endothelial cells, the TNF-induced phosphorylation and activation of cytosolic PLA2 and the IL-1-stimulated synthesis of collagenase and stromelysin. These and additional data demonstrate that CSBP/p38 is involved not only cytokine synthesis, but also in cytokine signaling [CSBP/P38 kinase reviewed in Cohen, P. *Trends Cell Biol.*, 353–361(1997)].

Interleukin-1 (IL-1) and Tumor Necrosis Factor (TNF) are biological substances produced by a variety of cells, such as monocytes or macrophages. IL-1 has been demonstrated to mediate a variety of biological activities thought to be important in immunoregulation and other physiological conditions such as inflammation [See, e.g., Dinarello et al., Rev. Infect. Disease, 6, 51 (1984)]. The myriad of known biological activities of IL-1 include the activation of T helper cells, induction of fever, stimulation of prostaglandin or collagenase production, neutrophil chemotaxis, induction of acute phase proteins and the suppression of plasma iron levels.

There are many disease states in which excessive or unregulated IL-1 production is implicated in exacerbating and/or causing the disease. These include rheumatoid arthritis, osteoarthritis, endotoxemia and/or toxic shock syndrome, other acute or chronic inflammatory disease states such as the inflammatory reaction induced by endotoxin or inflammatory bowel disease; tuberculosis, atherosclerosis, muscle degeneration, cachexia, psoriatic arthritis, Reiter's syndrome, rheumatoid arthritis, gout, traumatic arthritis, rubella arthritis, and acute synovitis. Recent evidence also links IL-1 activity to diabetes and pancreatic β cells [review of the biological activities which have been attributed to IL-1 Dinarello, *J. Clinical Immunology*, 5 (5), 287–297 (1985)].

Excessive or unregulated TNF production has been implicated in mediating or exacerbating a number of diseases including rheumatoid arthritis, rheumatoid spondylitis, osteoarthritis, gouty arthritis and other arthritic conditions; sepsis, septic shock, endotoxic shock, gram negative sepsis, toxic shock syndrome, adult respiratory distress syndrome, cerebral malaria, chronic pulmonary inflammatory disease, silicosis, pulmonary sarcoisosis, bone resorption diseases, reperfusion injury, graft vs. host reaction, allograft rejections, fever and myalgias due to infection, such as influenza, cachexia secondary to infection or malignancy, cachexia, secondary to acquired immune deficiency syndrome (AIDS), AIDS, ARC (AIDS related complex), keloid formation, scar tissue formation, Crohn's disease, ulcerative colitis, or pyresis.

Interleukin-8 (IL-8) is a chemotactic factor produced by several cell types including mononuclear cells, fibroblasts, endothelial cells, and keratinocytes. Its production from endothelial cells is induced by IL-1, TNF, or lipopolysaccharide (LPS). IL-8 stimulates a number of functions in vitro. It has been shown to have chemoattractant properties for neutrophils, T-lymphocytes, and basophils. In addition it induces histamine release from basophils from both normal and atopic individuals as well as lysozomal enzyme release and respiratory burst from neutrophils. IL-8 has also been shown to increase the surface expression of Mac-1 (CD11b/CD18) on neutrophils without de novo protein synthesis, this may contribute to increased adhesion of the neutrophils to vascular endothelial cells. Many diseases are characterized by massive neutrophil infiltration. Conditions associated with an increased in IL-8 production (which is responsible for chemotaxis of neutrophil into the inflammatory site) would benefit by compounds which are suppressive of IL-8 production.

IL-1 and TNF affect a wide variety of cells and tissues and these cytokines as well as other leukocyte derived cytokines are important and critical inflammatory mediators of a wide variety of disease states and conditions. The inhibition of these cytokines is of benefit in controlling, reducing and alleviating many of these disease states.

Inhibition of signal transduction via CSBP/p38, which in addition to IL-1, TNF and IL-8 described above is also required for the synthesis and/or action of several additional pro-inflammatory proteins (i.e., IL-6, GM-CSF, COX-2, collagenase and stromelysin), is expected to be a highly effective mechanism for regulating the excessive and destructive activation of the immune system. This expectation is supported by the potent and diverse anti-inflammatory activities described for CSBP/p38 kinase inhibitors [Badger, et al., *J. Pharm. Exp. Thera.* 279 (3): 1453–1461 (1996); Griswold, et al., *Pharmacol. Comm.* 7, 323–229 (1996)].

There remains a need for treatment in this field, for compounds which are cytokine suppressive anti-inflammatory drugs, i.e. compounds which are capable of inhibiting the CSBP/p38/RK kinase.

BRIEF DESCRIPTION OF THE DRAWINGS

FIG. 1 demonstrates the mitogen-activated protein kinase (MAP) kinase cascade.

FIG. 2 demonstrates the p38 kinase pathway.

SUMMARY OF THE INVENTION

This invention relates to the novel compounds of Formula (I) and (II) and pharmaceutical compositions comprising a compound of Formula (I) or (II) and a pharmaceutically acceptable diluent or carrier.

This invention relates to a method of treating a CSBP/RK/p38 kinase mediated disease in a mammal in need thereof, which method comprises administering to said mammal an effective amount of a compound of Formula (I) or (II).

This invention also relates to a method of inhibiting cytokines and the treatment of a cytokine mediated disease, in a mammal in need thereof, which comprises administering to said mammal an effective amount of a compound of Formula (I) or (II).

This invention more specifically relates to a method of inhibiting the production of IL-1 in a mammal in need thereof which comprises administering to said mammal an effective amount of a compound of Formula (I) or (II).

This invention more specifically relates to a method of inhibiting the production of IL-6 in a mammal in need thereof which comprises administering to said mammal an effective amount of a compound of Formula (I) or (II).

This invention more specifically relates to a method of inhibiting the production of IL-8 in a mammal in need thereof which comprises administering to said mammal an effective amount of a compound of Formula (I) or (II).

This invention more specifically relates to a method of inhibiting the production of TNF in a mammal in need thereof which comprises administering to said mammal an effective amount of a compound of Formula (I) or (II).

Accordingly, the present invention provides for a compound of the formula:

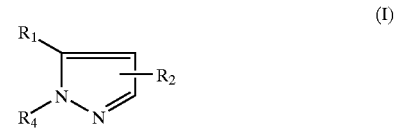

(I)

wherein $R_1$ is 4-pyridyl, 4-pyrimidinyl, 4-pyridazinyl, 1,2,4-triazin-5-yl, 4-quinolyl, 6-isoquinol, or quinazolin-4-yl ring, which ring is optionally substituted independently one to three times with Y, $NHR_a$, optionally substituted $C_{1-4}$ alkyl, halogen, hydroxyl, optionally substituted $C_{1-4}$ alkoxy, optionally substituted $C_{1-4}$ alkylthio, optionally substituted $C_{1-4}$ alkylsulfinyl, $CH_2OR_{12}$, amino, mono and di-$C_{1-6}$ alkyl substituted amino, $N(R_{10})C(O)R_b$, $N(R_{10})S(O)_2R_d$, or an N-heterocyclyl ring which ring has from 5 to 7 members and optionally contains an additional heteroatom selected from oxygen, sulfur or $NR_{15}$;

Y is $X_1$—$R_a$;

$X_1$ is sulfur or oxygen;

$R_a$ is $C_{1-6}$alkyl, aryl, aryl$C_{1-6}$alkyl, heterocyclic, heterocyclyl$C_{1-6}$ alkyl, heteroaryl, or heteroaryl$C_{1-6}$alkyl, wherein each of these moieties may be optionally substituted;

$R_b$ is hydrogen, $C_{1-6}$ alkyl, $C_{3-7}$ cycloalkyl, aryl, aryl$C_{1-4}$ alkyl, heteroaryl, heteroaryl$C_{1-4}$alkyl, heterocyclyl, or heterocyclyl$C_{1-4}$ alkyl;

$R_d$ is $C_{1-6}$ alkyl, $C_{3-7}$ cycloalkyl, aryl, aryl$C_{1-4}$ alkyl, heteroaryl, heteroaryl$C_{1-4}$alkyl, heterocyclyl, or heterocyclyl$C_{1-4}$ alkyl;

$R_4$ is phenyl, naphth-1-yl or naphth-2-yl, or heteroaryl, which is optionally substituted by one to three substituents, each of which is independently selected, and which, for a 4-phenyl, 4-naphth-1-yl, 5-naphth-2-yl or 6-naphth-2-yl substituent, is halogen, cyano, nitro, C(Z) $NR_7R_{17}$, $C(Z)OR_{16}$, $(CR_{10}R_{20})_vCOR_{12}$, $SR_5$, $S(O)R_5$, $OR_{12}$, halo-substituted-$C_{1-4}$ alkyl, $C_{1-4}$ alkyl, $ZC(Z)R_{12}$, $NR_{10}C(Z)R_{16}$, or $(CR_{10}R_{20})_vNR_{10}R_{20}$ and which, for other positions of substitution, is halogen, cyano, nitro, phenyl, —C(Z)NR$_{13}$R$_{14}$, C(Z)OR$_3$, (CR$_{10}$R$_{20}$)$_{m''}$COR$_3$, S(O)$_m$R$_3$, OR$_3$, halo-substituted-C$_{1-4}$ alkyl, C$_{1-10}$ alkyl, ZC(Z)R$_3$, optionally substituted phenyl, (CR$_{10}$R$_{20}$)$_{m''}$NR$_{10}$C(Z)R$_3$, NR$_{10}$S(O)$_m$R$_8$, NR$_{10}$S(O)$_m$NR$_7$R$_{17}$, or (CR$_{10}$R$_{20}$)$_{m''}$NR$_{13}$R$_{14}$;

n is 0, or an integer having a value of 1 to 10;

v is 0, or an integer having a value of 1 or 2;

m is 0, or the integer 1 or 2;

m' is an integer having a value of 1 or 2, m" is 0, or an integer having a value of 1 to 5;

R$_2$ is hydrogen, (CR$_{10}$R$_{23}$)$_n$OR$_9$, (CR$_{10}$R$_{23}$)$_n$OR$_{11}$, C$_{1-10}$alkyl, halo-substituted C$_{1-10}$ alkyl, C$_{2-10}$ alkenyl, C$_{2-10}$ alkynyl, C$_{3-7}$ cycloalkyl, C$_{3-7}$cycloalkylC$_{1-10}$ alkyl, C$_{5-7}$ cycloalkenyl, C$_{5-7}$ cycloalkenyl C$_{1-10}$alkyl, aryl, arylC$_{1-10}$ alkyl, heteroaryl, heteroarylC$_{1-10}$alkyl, heterocyclyl, heterocyclylC$_{1-10}$ alkyl, (CR$_{10}$R$_{23}$)$_n$S(O)$_m$R$_{18}$, (CR$_{10}$R$_{23}$)$_n$NHS(O)$_2$R$_{18}$, (CR$_{10}$R$_{23}$)$_n$NR$_{13}$R$_{14}$, (CR$_{10}$R$_{23}$)$_n$NO$_2$, (CR$_{10}$R$_{23}$)$_n$CN, (CR$_{10}$R$_{23}$)$_n$S(O)$_{m'}$NR$_{13}$R$_{14}$, (CR$_{10}$R$_{230}$)$_n$C(Z)R$_{11}$, (CR$_{10}$R$_{23}$)$_n$OC(Z)R$_{11}$, (CR$_{10}$R$_{23}$)$_n$C(Z)OR$_{11}$, (CR$_{10}$R$_{23}$)$_n$C(Z)NR$_{13}$R$_{14}$, (CR$_{10}$R$_{23}$)$_n$C(Z)NR$_{11}$OR$_9$, (CR$_{10}$R$_{23}$)$_n$NR$_{10}$C(Z)R$_{11}$, (CR$_{10}$R$_{23}$)$_n$NR$_{10}$C(Z)NR$_{13}$R$_{14}$, (CR$_{10}$R$_{23}$)$_n$N(OR$_6$)C(Z)NR$_{13}$R$_{14}$, (CR$_{10}$R$_{23}$)$_n$N(OR$_6$)C(Z)R$_{11}$, (CR$_{10}$R$_{23}$)$_n$C(=NOR$_6$)R$_{11}$, (CR$_{10}$R$_{23}$)$_n$NR$_{10}$C(=NR$_{19}$)NR$_{13}$R$_{14}$, (CR$_{10}$R$_{23}$)$_n$OC(Z)NR$_{13}$R$_{14}$, (CR$_{10}$R$_{23}$)$_n$NR$_{10}$C(Z)NR$_{13}$R$_{14}$, (CR$_{10}$R$_{23}$)$_n$NR$_{10}$C(Z)OR$_{10}$, 5-(R$_{18}$)-1,2,4-oxadizaol-3-yl or 4-(R$_{12}$)-5-(R$_{18}$R$_{19}$)-4,5-dihydro-1,2,4-oxadiazol-3-yl; wherein the cycloalkyl, cycloalkyl alkyl, aryl, arylalkyl, heteroaryl, heteroaryl alkyl, heterocyclic and heterocyclic alkyl groups may be optionally substituted;

R$_3$ is heterocyclyl, heterocyclylC$_{1-10}$ alkyl or R$_8$;

R$_5$ is hydrogen, C$_{1-4}$ alkyl, C$_{2-4}$ alkenyl, C$_{2-4}$ alkynyl or NR$_7$R$_{17}$, excluding the moieties SR$_5$ being SNR$_7$R$_{17}$ and SOR$_5$ being SOH;

R$_6$ is hydrogen, a pharmaceutically acceptable cation, C$_{1-10}$ alkyl, C$_{3-7}$ cycloalkyl, aryl, arylC$_{1-4}$ alkyl, heteroaryl, heteroarylC$_{1-4}$ alkyl, heterocyclic, aroyl, or C$_{1-10}$ alkanoyl;

R$_7$ and R$_{17}$ is each independently selected from hydrogen or C$_{1-4}$ alkyl or R$_7$ and R$_{17}$ together with the nitrogen to which they are attached form a heterocyclic ring of 5 to 7 members which ring optionally contains an additional heteroatom selected from oxygen, sulfur or NR$_{15}$;

R$_8$ is C$_{1-10}$ alkyl, halo-substituted C$_{1-10}$ alkyl, C$_{2-10}$ alkenyl, C$_{2-10}$ alkynyl, C$_{3-7}$ cycloalkyl, C$_{5-7}$ cycloalkenyl, aryl, arylC$_{1-10}$ alkyl, heteroaryl, heteroarylC$_{1-10}$ alkyl, (CR$_{10}$R$_{20}$)$_n$OR$_{11}$, (CR$_{10}$R$_{20}$)$_n$S(O)$_m$R$_{18}$, (CR$_{10}$R$_{20}$)$_n$NHS(O)$_2$R$_{18}$, (CR$_{10}$R$_{20}$)$_n$NR$_{13}$R$_{14}$; wherein the aryl, arylalkyl, heteroaryl, heteroaryl alkyl may be optionally substituted;

R$_9$ is hydrogen, C(Z)R$_{11}$ or optionally substituted C$_{1-10}$ alkyl, S(O)$_2$R$_{18}$, optionally substituted aryl or optionally substituted aryl-C$_{1-4}$ alkyl;

R$_{10}$ and R$_{20}$ is each independently selected from hydrogen or C$_{1-4}$ alkyl;

R$_{11}$ is hydrogen, C$_{1-10}$ alkyl, C$_{3-7}$ cycloalkyl, heterocyclyl, heterocyclyl C$_{1-10}$alkyl, aryl, arylC$_{1-10}$ alkyl, heteroaryl or heteroarylC$_{1-10}$ alkyl, wherein the aryl, arylalkyl, heteroaryl, heteroaryl alkyl, heterocyclyl or heterocyclylalkyl, may be optionally substituted;

R$_{12}$ is hydrogen or R$_{16}$;

R$_{13}$ and R$_{14}$ is each independently selected from hydrogen or optionally substituted C$_{1-4}$ alkyl, optionally substituted aryl or optionally substituted aryl-C$_{1-4}$ alkyl, or together with the nitrogen which they are attached form a heterocyclic ring of 5 to 7 members which ring optionally contains an additional heteroatom selected from oxygen, sulfur or NR$_9$;

R$_{15}$ is hydrogen, C$_{1-4}$ alkyl or C(Z)—C$_{1-4}$ alkyl;

R$_{16}$ is C$_{1-4}$ alkyl, halo-substituted-C$_{1-4}$ alkyl, or C$_{3-7}$ cycloalkyl;

R$_{18}$ is C$_{1-10}$ alkyl, C$_{3-7}$ cycloalkyl, heterocyclyl, aryl, arylC$_{1-10}$ alkyl, heterocyclyl, heterocyclyl-C$_{1-10}$alkyl, heteroaryl or heteroarylalkyl, wherein the aryl, arylalkyl, heteroaryl, heteroaryl alkyl, heterocyclyl or heterocyclylalkyl may be optionally substituted;

R$_{19}$ is hydrogen, cyano, C$_{1-4}$ alkyl, C$_{3-7}$ cycloalkyl or aryl;

R$_{23}$ is hydrogen, C$_{1-6}$ alkyl, C$_{3-7}$ cycloalkyl, aryl, arylC$_{1-4}$ alkyl, heteroaryl, heteroarylC$_{1-4}$alkyl, heterocyclyl, or heterocyclylC$_{1-4}$ alkyl moiety, all of which may be optionally substituted;

Z is oxygen or sulfur;

provided that when R$_1$ is a 4-pyridyl, R$_4$ is a 4-NH$_2$S(O)$_2$ phenyl, then R$_2$ is other than a 3-position trifluoromethyl group;

or a pharmaceutically acceptable salt thereof.

DETAILED DESCRIPTION OF THE INVENTION

The novel compounds of Formula (I) or (II) may also be used in association with the veterinary treatment of mammals, other than humans, in need of inhibition of cytokine inhibition or production. In particular, cytokine mediated diseases for treatment, therapeutically or prophylactically, in animals include disease states such as those noted herein in the Methods of Treatment section, but in particular viral infections. Examples of such viruses include, but are not limited to, lentivirus infections such as, equine infectious anaemia virus, caprine arthritis virus, visna virus, or maedi virus or retrovirus infections, such as but not limited to feline immunodeficiency virus (FIV), bovine immunodeficiency virus, or canine immunodeficiency virus or other retroviral infections.

In Formula (I), suitable R$_1$ moieties includes 4-pyridyl, 4-pyrimidinyl, 4-pyridazinyl, 1,2,4-triazin-5-yl, 4-quinolyl, 6-isoquinolinyl, or 4-quinazolinyl, of which the 4-pyridyl, or 4-pyrimidinyl are preferred. A preferred ring placement of the R$_1$ substituent on the 4-pyridyl derivative is the 2-position, such as in 2-methoxy-4-pyridyl. A preferred ring placement on the 4-pyrimidinyl ring is also at the 2-position, such as in 2-methoxy-pyrimidinyl.

A preferred embodiment of Formula (I) is where R$_1$ is an optionally substituted 4-pyridazinyl or 1,2,4-triazin-5-yl ring, substituted as defined above in formula (I).

Suitable additional substituents for the R$_1$ heteroaryl rings are Y, NHR$_a$, optionally substituted C$_{1-4}$ alkyl, halogen, hydroxyl, optionally substituted C$_{1-4}$ alkoxy, optionally substituted C$_{1-4}$ alkylthio, optionally substituted C$_{1-4}$ alkylsulfinyl, CH$_2$ OR$_{12}$, amino, mono and di- C$_{1-6}$ alkyl substituted amino, N(R$_{10}$)C(O)R$_b$; N(R$_{10}$)S(O)$_2$R$_d$; or an N-heterocyclyl ring which ring has from 5 to 7 members and optionally contains an additional heteroatom selected from oxygen, sulfur or NR$_{15}$.

Suitably Y is X$_1$—R$_a$; and X$_1$ is oxygen or sulfur, preferably oxygen.

Suitably R$_a$ is C$_{1-6}$alkyl, aryl, arylC$_{1-6}$alkyl, heterocyclic, heterocyclylC$_{1-6}$ alkyl, heteroaryl, or heteroarylC$_{1-6}$alkyl, wherein each of these moieties may be optionally substituted as defined herein.

When Ra is aryl, it is preferably phenyl or naphthyl. When R$_a$ is an arylC$_{1-6}$alkyl, it is preferably benzyl or napthylmethyl. When $R_a$ is a heterocyclic or heterocyclyl$C_{1-6}$ alkyl moiety, the heterocyclic portion is preferably pyrrolindinyl, piperazine, piperidine, morpholino, tetrahydropyran, tetrahydrothiopyranyl, tetrahydrothiopyran-sulfinyl, tetrahydrothio-pyransulfonyl, pyrrolindinyl, indole, or piperonyl. It is noted that the heterocyclic rings herein may contain unsaturation, such as in an indole ring. When $R_a$ is a heteroaryl or heteroarylalkyl moiety it is as defined herein in the definition section.

The $R_a$ aryl, heterocyclic and heteroaryl containing rings may also be optionally substituted one or more times independently, preferably 1 to 3 times, with halogen, such as fluoro or chloro, $C_{1-4}$ alkyl, such as methyl, ethyl, propyl, isopropyl, or t-butyl; halosubstituted alkyl, such as $CF_3$; hydroxy; hydroxy substituted $C_{1-4}$ alkyl; $C_{1-4}$ alkoxy, such as methoxy or ethoxy; $S(O)_m$alkyl and $S(O)m$ aryl; $C(O)OR_{11}$, such as $C(O)C_{1-4}$ alkyl or $C(O)OH$ moieties; $C(O)R_{11}$; $OC(O)R_c$; $O-(CH_2)_s-O-$, such as in a ketal or dioxyalkylene bridge, and s is 1 to 3; amino; $NR_{13}N_{14}$; $N(R_{10})C(O)R_b$; $N(R_{10})S(O)_2R_d$; $C(O)NR_{10}R_{20}$; $S(O)_2(CR_{10}R_{20})_tNR_{13}R_{14}$ (wherein t is 0, or an integer of 1 to 3); cyano; nitro; aryl, such as phenyl; an optionally substituted aryl$C_{1-6}$alkyl, such as benzyl or phenethyl; aryloxy, such as phenoxy; or aryl$C_{1-6}$alkyloxy such as benzyloxy.

Suitably, $R_b$ is hydrogen, $C_{1-6}$ alkyl, $C_{3-7}$ cycloalkyl, aryl, aryl$C_{1-4}$ alkyl, heteroaryl, heteroaryl$C_{1-4}$alkyl, heterocyclyl, or heterocyclyl$C_{1-4}$ alkyl, wherein all of these moieties may be optionally substituted.

Suitably, $R_c$ is hydrogen, optionally substituted $C_{1-6}$ alkyl, $C_{3-7}$ cycloalkyl, aryl, aryl$C_{1-4}$ alkyl, heteroaryl, heteroaryl$C_{1-4}$alkyl, heterocyclyl, or heterocyclyl$C_{1-4}$ alkyl moiety, wherein all of these moieties may be optionally substituted.

Suitably, $R_d$ is $C_{1-6}$ alkyl, $C_{3-7}$ cycloalkyl, aryl, aryl$C_{1-4}$ alkyl, heteroaryl, heteroaryl$C_{1-4}$alkyl, heterocyclyl, or heterocyclyl$C_{1-4}$ alkyl, wherein all of these moieties may be optionally substituted.

When the $R_a$ moiety is an alkyl group it may be optionally substituted as defined herein in the definition section below. Also, the alkyl portion of the $R_1$ substituents, where applicable, such as the mono- and di-$C_{1-6}$ alkyl amino moieties, may also be halo substituted.

Preferably, the $R_a$ group is an alkyl, such as methyl, an optionally substituted aryl, such as phenyl, or an optionally substituted arylalkyl, such as benzyl.

When the $R_1$ optional substituent group is $N(R_{10})C(O)R_b$, $R_b$ is preferably a $C_{1-6}$ alkyl; and $R_{10}$ is preferably hydrogen. It is also recognized that all the $R_b$ moieties, in particular the $C_{1-6}$ alkyl group may be optionally substituted, preferably from one to three times as defined herein. Preferably $R_b$ is $C_{1-6}$ alkyl substituted with halogen, such as fluorine, as in trifluoromethyl or trifluroethyl.

Suitably, $R_4$ is phenyl, naphth-1-yl or naphth-2-yl, a heteroaryl ring or a fused phenyl containing ring system. Preferably, $R_4$ is a phenyl or naphthyl ring.

Suitable substitutions for $R_4$ when this is a 4-phenyl, 4-naphth-1-yl, 5-naphth-2-yl or 6-naphth-2-yl moiety are one to three, preferably one to two, substituents each of which are independently selected from halogen, $SR_5$, $SOR_5$, $OR_{12}$, $CF_3$, or $(CR_{10}R_{20})_vNR_{10}R_{20}$, and for other positions of substitution on these rings preferred substitution is halogen, $S(O)_mR_3$, $OR_3$, $CF_3$, $(CR_{10}R_{20})_m$"$NR_{13}R_{14}$, $NR_{10}C(Z)R_3$ and $NR_{10}S(O)_m$"$R_8$. Preferred substituents for the 4-position in phenyl and naphth-1-yl and on the 5-position in naphth-2-yl include halogen, especially fluoro and chloro, and $SR_5$ and $SOR_5$ wherein $R_5$ is preferably a $C_{1-2}$ alkyl, more preferably methyl; of which the fluoro and chloro is more preferred, and most especially preferred is fluoro. For all other substituents, including the heteroaryl ring(s) and fused phenyl ring systems, or the 3-position in phenyl and naphth-1-yl rings, the substituents are independently selected from halogen, especially fluoro and chloro; $OR_3$, especially $C_{1-4}$ alkoxy; $CF_3$, $NR_{10}R_{20}$, such as amino; $NR_{10}C(Z)R_3$, especially $NHCO(C_{1-10}$ alkyl); $NR_{10}S(O)_{m'}R_8$, especially $NHSO_2(C_{1-10}$ alkyl); and $SR_3$ and $SOR_3$ wherein $R_3$ is preferably a $C_{1-2}$ alkyl, more preferably methyl.

When the phenyl ring is disubstituted, preferably it is two independent halogen moieties, such as fluoro and chloro, preferably di-chloro and more preferably in the 3,4-position. It is also preferred that for the 3-position of both the $OR_3$ and $ZC(Z)R_3$ moieties, that the $R_3$ may also include hydrogen.

Preferably, the $R_4$ moiety is an unsubstituted or substituted phenyl moiety. More preferably, $R_4$ is phenyl or phenyl substituted at the 4-position with fluoro and/or substituted at the 3-position with fluoro, chloro, $C_{1-4}$ alkoxy, methanesulfonamido or acetamido, or $R_4$ is a phenyl di-substituted at the 3,4-position independently with chloro or fluoro, more preferably chloro. Most preferably, $R_4$ is 4-fluorophenyl. Preferably $R_4$ is not substituted with $S(O)_2R_3$ when $R_3$ is $NR_{13}NR_{14}$, and $R_{13}$ and $R_{14}$ are hydrogen, yielding the moiety $NH_2S(O)_2-$ in the 4-position.

The $R_4$ substituent may also include a fused phenyl containing ring system, i.e. a benzene ring fused to a second 4–7 membered carboxylic or heterocyclic ring (containing one or more of O/S/N) which additional ring may not be aromatic, i.e. it can contain some unsaturation. This fused ring system can include such rings as a tetrahydronapthalene ring, an indoline ring, an indole or a benzimidazole ring system.

In Formula (I), Z is Suitably Oxygen or Sulfur.

Suitably, $R_2$ is hydrogen, $(CR_{10}R_{23})_nOR_9$, $(CR_{10}R_{23})_nOR_{11}$, $C_{1-10}$alkyl, halo-substituted $C_{1-10}$ alkyl, $C_{2-10}$ alkenyl, $C_{2-10}$ alkynyl, $C_{3-7}$ cycloalkyl, $C_{3-7}$cycloalkyl$C_{1-10}$ alkyl, $C_{5-7}$ cycloalkenyl, $C_{5-7}$ cycloalkenyl $C_{1-10}$alkyl, aryl, aryl$C_{1-10}$ alkyl, heteroaryl, heteroaryl$C_{1-10}$alkyl, heterocyclyl, heterocyclyl$C_{1-10}$ alkyl, $(CR_{10}R_{23})_nS(O)_mR_{18}$, $(CR_{10}R_{23})_nNHS(O)_2R_{18}$, $(CR_{10}R_{23})_nNR_{13}R_{14}$, $(CR_{10}R_{23})_nNO_2$, $(CR_{10}R_{23})_nCN$, $(CR_{10}R_{23})_nS(O)_{m'}NR_{13}R_{14}$, $(CR_{10}R_{23})_nC(Z)R_{11}$, $(CR_{10}R_{23})_nOC(Z)R_{11}$, $(CR_{10}R_{23})_nC(Z)OR_{11}$, $(CR_{10}R_{23})_nC(Z)NR_{13}R_{14}$, $(CR_{10}R_{23})_nC(Z)NR_{11}OR_9$, $(CR_{10}R_{23})_nNR_{10}C(Z)R_{11}$, $(CR_{10}R_{23})_nNR_{10}C(Z)NR_{13}R_{14}$, $(CR_{10}R_{23})_nN(OR_6)C(Z)NR_{13}R_{14}$, $(CR_{10}R_{23})_nN(OR_6)C(Z)R_{11}$, $(CR_{10}R_{23})_nC(=NOR_6)R_{11}$, $(CR_{10}R_{23})_nNR_{10}C(=NR_{19})NR_{13}R_{14}$, $(CR_{10}R_{23})_nOC(Z)NR_{13}R_{14}$, $(CR_{10}R_{23})_nNR_{10}C(Z)NR_{13}R_{14}$, $(CR_{10}R_{23})_nNR_{10}C(Z)OR_{10}$, 5-$(R_{18})$-1,2,4-oxadizaol-3-yl or 4-$(R_{12})$-5-$(R_{18}R_{19})$-4,5-dihydro-1,2,4-oxadiazol-3-yl; wherein the cycloalkyl, cycloalkylalkyl, aryl, arylalkyl, heteroaryl, heteroaryl alkyl, heterocyclic and heterocyclic alkyl groups may be optionally substituted.

Suitably, $R_{23}$ is hydrogen, $C_{1-6}$ alkyl, $C_{3-7}$ cycloalkyl, aryl, aryl$C_{1-4}$ alkyl, heteroaryl, heteroaryl$C_{1-4}$alkyl, heterocyclyl, or heterocyclyl$C_{1-4}$ alkyl moiety, all of which may be optionally substituted as defined below.

Preferably, $R_2$ is hydrogen, an optionally substituted heterocyclyl ring, and optionally substituted heterocyclyl-$C_{1-10}$ alkyl, an optionally substituted $C_{1-10}$ alkyl, an optionally substituted $C_{3-7}$cycloalkyl, an optionally substituted $C_{3-7}$cycloalkyl $C_{1-10}$ alkyl, $(CR_{10}R_{23})_nC(Z)OR_{11}$ group, $(CR_{10}R_{23})_nNR_{13}R_{14}$, $CR_{10}R_{23})_nNHS(O)_2R_{18}$, $(CR_{10}R_{23})_nS$ $(O)_mR_{18}$, an optionally substituted aryl; an optionally substituted $arylC_{1-10}$ alkyl, $(CR_{10}R_{23})_nOR_{11}$, $(CR_{10}R_{23})_nC(Z)R_{11}$, or $(CR_{10}R_{23})_nC(=NOR_6)R_{11}$ group.

Preferably, $R_2$ is selected from hydrogen, $C_{1-10}$ alkyl, optionally substituted heterocyclyl, optionally substituted heterocyclyl$C_{1-10}$ alkyl, $(CR_{10}R_{23})_nNS(O)_2R_{18}$, $CR_{10}R_{23})_n S(O)_m R_{18}$, $arylC_{1-10}$ alkyl, $(CR_{10}R_{23})_nNR_{13}R_{14}$, optionally substituted $C_{3-7}$cycloalkyl, or optionally substituted $C_{3-7}$cycloalkyl $C_{1-10}$ alkyl.

For compounds of Formula (I) only, when $R_2$ is substituted in the 3-position, than $R_2$ is other than a halosubstituted alkyl, such as $CF_3$. Suitably, when $R_1$ is a 4-pyridyl, and $R_4$ is a 4-$NH_2S(O)_2$phenyl, then $R_2$ is other than a 3-position trifluoromethyl group;

When $R_2$ is an optionally substituted heterocyclyl, the ring is preferably a morpholino, pyrrolidinyl, piperazinyl, or a piperidinyl group. When the ring is optionally substituted, the substituents may be directly attached to the free nitrogen, such as in the piperidinyl group or pyrrole ring, or on the ring itself. Preferably the ring is a piperidine or pyrrole, more preferably piperidine. The heterocyclyl ring may be optionally substituted one to four times independently by halogen; $C_{1-4}$ alkyl; aryl, such as phenyl; aryl alkyl, such as benzyl—wherein the aryl or aryl alkyl moieties themselves may be optionally substituted (as in the definition section below); $C(O)OR_{11}$, such as the $C(O)C_{1-4}$ alkyl or $C(O)OH$ moieties; $C(O)H$; $C(O)C_{1-4}$ alkyl, hydroxy substituted $C_{1-4}$ alkyl, $C_{1-4}$ alkoxy, $S(O)_mC_{1-4}$ alkyl, or $NR_{10}R_{20}$.

Preferably if the ring is a piperidine, the substituents are directly attached on the available nitrogen, i.e. a 1-Formyl-4-piperidine, 1-benzyl-4-piperidine, 1-methyl-4-piperidine, 1-ethoxycarbonyl-4-piperidine. If the ring is substituted by an alkyl group and the ring is attached in the 4-position, it is preferably substituted in the 2- or 6-position or both, such as 2,2,6,6-tetramethyl-4-piperidine.

When $R_2$ is an optionally substituted heterocyclyl $C_{1-10}$ alkyl group, the ring is preferably a morpholino, pyrrolidinyl, piperazinyl or a piperidinyl group. Preferably the alkyl chain is 1 to 4 carbons, more preferably 3 or 4, and most preferably 3, such as in a propyl group. Preferred heterocyclic alkyl groups include but are not limited to, morpholino ethyl, morpholino propyl, pyrrolidinyl propyl, and piperidinyl propyl moieties.

When $R_2$ is an optionally substituted $C_{3-7}$cycloalkyl, or an optionally substituted $C_{3-7}$cycloalkyl $C_{1-10}$ alkyl, the cycloalkyl group is preferably a $C_3$ or $C_6$ ring, most preferably a $C_6$ ring, which rings may be optionally substituted. The cycloalkyl rings may be optionally substituted one to three times independently by halogen, such as fluorine, chlorine, bromine or iodine; hydroxy; $OC(O)R_b$, $C_{1-10}$ alkoxy, such as methoxy or ethoxy; $S(O)_m$ alkyl, such as methylthio, methylsulfinyl or methylsulfonyl; $S(O)_m$aryl; cyano, nitro; $NR_7R_{17}$; $N(R_{10})C(O)X_1$ and $X_1$ is $C_{1-4}$ alkyl, aryl or aryl$C_{1-4}$alkyl; $C_{1-10}$ alkyl, such as methyl, ethyl, propyl, isopropyl, or t-butyl; optionally substituted alkyl wherein the substituents are halogen, (such as $CF_3$), hydroxy, nitro, cyano, amino, $NR_7R_{17}$, $S(O)_m$ alkyl and $S(O)m$ aryl; optionally substituted alkylene, such as ethylene or propylene; optionally substituted alkyne, such as ethyne; $C(O)OR_{11}$, such as the free acid or methyl ester derivative; the group $R_e$; $C(O)H$; =O; =N—$OR_{11}$; N(H)—OH (or substituted alkyl or aryl derivatives thereof on the nitrogen or the oxime moiety); $N(OR_f)$—$C(O)$—$R_{21}$; an optionally substituted aryl, such as phenyl; an optionally substituted aryl$C_{1-4}$alkyl, such as benzyl or phenethyl; an optionally substituted heterocyclyl or heterocyclic $C_{1-4}$alkyl, and further wherein these aryl, arylalkyl, heterocyclic, and heterocyclic alkyl containing moieties are also optionally substituted one to two times by halogen, hydroxy, $C_{1-10}$ alkoxy, $S(O)_m$ alkyl, cyano, nitro, amino, mono & di-substituted $C_{1-6}$amino, $C_{1-10}$ alkyl, or an halosubstituted $C_{1-10}$ alkyl.

Suitably $R_e$ is a 1,3-dioxyalkylene group of the formula —O—$(CH_2)_s$—O—, wherein s is 1 to 3, preferably s is 2 yielding a 1,3-dioxyethylene moiety, or ketal functionality.

Suitably $R_f$ is hydrogen, a pharmaceutically acceptable cation, aroyl or a $C_{1-10}$ alkanoyl group.

Suitably $R_{21}$ is $NR_{22}R_{24}$; alkyl $_{1-6}$; halosubstituted alkyl $_{1-6}$; hydroxy substituted alkyl $_{1-6}$; alkenyl $_{2-6}$; aryl or heteroaryl optionally substituted by halogen, alkyl$_{1-6}$, halosubstituted alkyl$_{1-6}$, hydroxyl, or alkoxy $_{1-6}$.

Suitably $R_{22}$ is H or alkyl$_{1-6}$.

Suitably $R_{24}$ is H, alkyl$_{1-6}$, aryl, benzyl, heteroaryl, alkyl substituted by halogen or hydroxyl, or phenyl substituted by a member selected from the group consisting of halo, cyano, alkyl$_{1-12}$, alkoxy$_{1-6}$, halosubstituted alkyl $_{1-6}$, alkylthio, alkylsulphonyl, or alkylsulfinyl; or $R_{22}$ and $R_{24}$ may together with the nitrogen to which they are attached form a ring having 5 to 7 members, which ring members may be optionally replaced by a heteroatom selected from oxygen, sulfur or nitrogen. The ring may be saturated or contain more than one unsaturated bond. Preferably $R_{21}$ is $NR_{22}R_{24}$ and $R_{22}$ and $R_{24}$ are preferably hydrogen.

When the $R_2$ cycloalkyl moiety is substituted by $NR_7R_{17}$ group, or $NR_7R_{17}$ $C_{1-10}$ alkyl group, and the $R_7$ and $R_{17}$ are as defined in Formula (I), the substituent is preferably an amino, amino alkyl, or an optionally substituted pyrrolidinyl moiety. In those cases where $NR_7R_{17}$ and $NR_{13}R_{14}$ together cyclize to form a 5 to 7 membered ring, it is noted that those rings may be optionally substituted 1 to 3 times as defined in the definition section.

A preferred position of ring substitution on the $C_6$ cycloalkyl moiety is the 4-position. When the cycloalkyl ring is di-substituted it is preferably di-substituted at the 4-position, such as in:

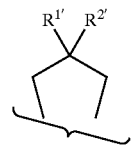

wherein $R^{1'}$ and $R^{2'}$ are independently the optional substituents indicated above for $R_2$.

Preferably, $R^{1'}$ and $R^{2'}$ are hydrogen, hydroxy, alkyl, substituted alkyl, optionally substituted alkyne, aryl, arylalkyl, $(CR_{10}R_{23})_nNR_7R_{17}$, and $N(R_{10})C(O)R_{11}$. Suitably, alkyl is $C_{1-4}$ alkyl, such as methyl, ethyl, or isopropyl; $NR_7R_{17}$ and $NR_7R_{17}$ alkyl, such as amino, methylamino, aminomethyl, aminoethyl; substituted alkyl such as in cyanomethyl, cyanoethyl, nitroethyl; pyrrolidinyl; aryl such as in phenyl; arylalkyl, such as in benzyl; optionally substituted alkyne, such as ethyne or propynyl; or together $R^{1'}$ and $R^{2'}$ are a keto functionality.

In all instances herein where there is an alkenyl or alkynyl moiety as a substituent group, the unsaturated linkage, i.e., the vinylene or acetylene linkage is preferably not directly attached to the nitrogen, oxygen or sulfur moieties, for instance in $OR_3$, or for certain $R_2$ moieties.

Suitable pharmaceutically acceptable salts are well known to those skilled in the art and include basic salts of inorganic and organic acids, such as hydrochloric acid, hydrobromic acid, sulphuric acid, phosphoric acid, methane sulphonic acid, ethane sulphonic acid, acetic acid, malic acid, tartaric acid, citric acid, lactic acid, succinic acid, fumaric acid, maleic acid, benzoic acid, salicylic acid, phenylacetic acid and mandelic acid. In addition, pharmaceutically acceptable salts of compounds of Formula (I) may also be formed with a pharmaceutically acceptable cation, for instance, if a substituent group comprises a carboxy moiety. Suitable pharmaceutically acceptable cations are well known to those skilled in the art and include alkaline, alkaline earth, ammonium and quaternary ammonium cations.

As used herein, "optionally substituted", unless specifically defined, shall mean such groups as halogen, such as fluorine, chlorine, bromine or iodine; hydroxy; hydroxy substituted $C_{1-10}$alkyl; $C_{1-10}$ alkoxy, such as methoxy or ethoxy; S(O)m alkyl, wherein m is 0, 1 or 2, such as methylthio, methylsulfinyl or methylsulfonyl; halosubstituted $C_{1-10}$ alkoxy; $NR_7R_{17}$; $C_{1-10}$ alkyl, cycloalkyl, or cycloalkyl alkyl group, such as methyl, ethyl, propyl, isopropyl, t-butyl, etc. or cyclopropyl methyl; halosubstituted $C_{1-10}$ alkyl, such $CF_3$; an optionally substituted aryl, such as phenyl, or an optionally substituted arylalkyl, such as benzyl or phenethyl, and wherein these aryl containing moieties may also be optionally substituted one to three times by halogen; hydroxy; hydroxy substituted alkyl; $C_{1-10}$ alkoxy; $S(O)_m$ alkyl; amino, mono & di-$C_{1-6}$ alkyl substituted amino; $C_{1-6}$ alkyl; or $CF_3$.

The following terms, as used herein, refer to:

"halo" or "halogens", include the halogens: chloro, fluoro, bromo and iodo.

"$C_{1-10}$alkyl" or "alkyl"—both straight and branched chain radicals of 1 to 10 carbon atoms, unless the chain length is otherwise limited, including, but not limited to, methyl, ethyl, n-propyl, iso-propyl, n-butyl, sec-butyl, iso-butyl, tert-butyl, n-pentyl and the like.

The term "cycloalkyl" is used herein to mean cyclic radicals, preferably of 3 to 8 carbons, including but not limited to cyclopropyl, cyclopentyl, cyclohexyl, and the like.

The term "cycloalkenyl" is used herein to mean cyclic radicals, preferably of 5 to 8 carbons, which have at least one bond including but not limited to cyclopentenyl, cyclohexenyl, and the like.

The term "alkenyl" is used herein at all occurrences to mean straight or branched chain radical of 2–10 carbon atoms, unless the chain length is limited thereto, including, but not limited to ethenyl, 1-propenyl, 2-propenyl, 2-methyl-1-propenyl, 1-butenyl, 2-butenyl and the like.

The term "aryl" is used herein to mean, phenyl and naphthyl.

The term "heteroaryl" (on its own or in any combination, such as "heteroaryloxy", or "heteroaryl alkyl") is used herein to mean a 5–10 membered aromatic ring system in which one or more rings contain one or more heteroatoms selected from the group consisting of N, O or S, such as, but not limited, to pyrrole, pyrazole, furan, thiophene, indole, quinoline, isoquinoline, quinazolinyl, pyridine, pyrimidine, oxazole, thiazole, thiadiazole, triazole, imidazole, or benzimidazole.

The term "heterocyclic" (on its own or in any combination, such as "heterocyclylalkyl") is used herein to mean a saturated or partially unsaturated 4–10 membered ring system in which one or more rings contain one or more heteroatoms selected from the group consisting of N, O, or S; such as, but not limited to, pyrrolidine, piperidine, piperazine, morpholine, tetrahydropyran, or imidazolidine.

The term "aralkyl" or "heteroarylalkyl" or "heterocyclicalkyl" is used herein to mean $C_{1-4}$ alkyl as defined above attached to an aryl, heteroaryl or heterocyclic moiety as also defined herein unless otherwise indicate.

The term "sulfinyl" is used herein to mean the oxide S (O) of the corresponding sulfide, the term "thio" refers to the sulfide, and the term "sulfonyl" refers to the fully oxidized $S(O)_2$ moiety.

The term "aroyl" is used herein to mean a C(O)Ar group, wherein Ar is as phenyl, naphthyl, or aryl $C_{1-4}$ alkyl derivative such as defined above, such group include but are note limited to benzyl and phenethyl.

The term "alkanoyl" is used herein to mean a $C(O)C_{1-10}$ alkyl wherein the alkyl is as defined above.

It is recognized that the compounds of the present invention may exist as stereoisomers, regioisomers, or diastereiomers. These compounds may contain one or more asymmetric carbon atoms and may exist in racemic and optically active forms. All of these compounds are included within the scope of the present invention.

Exemplified compounds of Formula (I) include:

4-[1-(4-Fluorophenyl)-3-phenyl-1H-pyrazol-5-yl]pyridine
4-[4-Bromo-1-(4-fluorophenyl)-3-phenyl-1H-pyrazol-5-yl]pyridine
4-[1-(4-Fluorophenyl)-3-[4-(methylthio)phenyl]-1H-pyrazol-5-yl]pyridine
4-[1-(4-Fluorophenyl)-3-[4-(methylsulfonyl)phenyl]-1H-pyrazol-5-yl]pyridine
4-[1-(4-Fluorophenyl)-3-[4-(methylsulfinyl)phenyl]-1H-pyrazol-5-yl]pyridine; or a pharmaceutically acceptable salt thereof.

Another aspect of the present invention are the novel compounds of Formula (II) as represented by the structure:

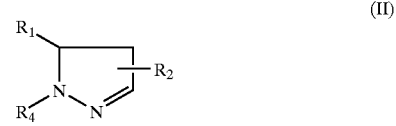

(II)

wherein $R_1$ is 4-pyridyl, 4-pyrimidinyl, 4-pyridazinyl, 4-triazin-5-yl, quinolyl, isoquinolinyl, or quinazolin-4-yl ring, which ring is optionally substituted independently one to three times with Y, $NHR_a$, optionally substituted $C_{1-4}$ alkyl, halogen, hydroxyl, optionally substituted $C_{1-4}$ alkoxy, optionally substituted $C_{1-4}$ alkylthio, optionally substituted $C_{1-4}$ alkylsulfinyl, $CH_2OR_{12}$, amino, mono and di-$C_{1-6}$ alkyl substituted amino, $N(R_{10})C(O)R_b$, $N(R_{10})S(O)_2R_d$ or an N-heterocyclyl ring which ring has from 5 to 7 members and optionally contains an additional heteroatom selected from oxygen, sulfur or $NR_{15}$;

Y is $X_1$—$R_a$;

$X_1$ is sulfur or oxygen;

$R_a$ is $C_{1-6}$alkyl, aryl, aryl$C_{1-6}$alkyl, heterocyclic, heterocyclyl$C_{1-6}$ alkyl, heteroaryl, or heteroaryl$C_{1-6}$alkyl, wherein each of these moieties may be optionally substituted;

$R_b$ is hydrogen, $C_{1-6}$ alkyl, $C_{3-7}$ cycloalkyl, aryl, aryl$C_{1-4}$ alkyl, heteroaryl, heteroaryl$C_{1-4}$alkyl, heterocyclyl, or heterocyclyl$C_{1-4}$ alkyl;

$R_d$ is $C_{1-6}$ alkyl, $C_{3-7}$ cycloalkyl, aryl, aryl$C_{1-4}$ alkyl, heteroaryl, heteroaryl$C_{1-4}$alkyl, heterocyclyl, or heterocyclyl$C_{1-4}$ alkyl;

$R_4$ is phenyl, naphth-1-yl or naphth-2-yl, a fused phenyl containing ring system or a heteroaryl, which is optionally substituted by one to three substituents, each of which is independently selected, and which, for a 4-phenyl, 4-naphth-1-yl, 5-naphth-2-yl or 6-naphth-2-yl substituent, is halogen, cyano, nitro, $C(Z)NR_7R_{17}$, $C(Z)OR_{16}$, $(CR_{10}R_{20})_vCOR_{12}$, $SR_5$, $SOR_5$, $OR_{12}$, halo-substituted-$C_{1-4}$ alkyl, $C_{1-4}$ alkyl, $ZC(Z)R_{12}$, $NR_{10}C(Z)R_{16}$, or $(CR_{10}R_{20})_vNR_{10}R_{20}$ and which, for other positions of substitution, is halogen, cyano, $C(Z)NR_{13}R_{14}$, $C(Z)OR_3$, $(CR_{10}R_{20})_{m''}COR_3$, $S(O)_mR_3$, $OR_3$, halo-substituted-$C_{1-4}$ alkyl, $C_{1-4}$ alkyl, $(CR_{10}R_{20})_{m''}NR_{10}C(Z)R_3$, $NR_{10}S(O)_{m'}R_8$, $NR_{10}S(O)_{m'}NR_7R_{17}$, $ZC(Z)R_3$ or $(CR_{10}R_{20})_{m''}NR_{13}R_{14}$;

n is 0, or an integer having a value of 1 to 10;
m is 0, or the integer 1 or 2;
m' is an integer having a value of 1 or 2,
m" is 0, or an integer having a value of 1 to 5;
v is 0, or an integer having a value of 1 or 2;

$R_2$ is hydrogen, $(CR_{10}R_{23})_n OR_9$, $(CR_{10}R_{23})_n OR_{11}$, $C_{1-10}$alkyl, halo-substituted $C_{1-10}$ alkyl, $C_{2-10}$ alkenyl, $C_{2-10}$ alkynyl, $C_{3-7}$ cycloalkyl, $C_{3-7}$cycloalkyl$C_{1-10}$ alkyl, $C_{5-7}$ cycloalkenyl, $C_{5-7}$ cycloalkenyl $C_{1-10}$alkyl, aryl, aryl$C_{1-10}$ alkyl, heteroaryl, heteroaryl$C_{1-10}$alkyl, heterocyclyl, heterocyclyl$C_{1-10}$ alkyl, $(C_{10}R_{23})_nS(O)_m R_{18}$, $(CR_{10}R_{23})_nNHS(O)_2R_{18}$, $(CR_{10}R_{23})_nNR_{13}R_{14}$, $(CR_{10}R_{23})_nNO_2$, $(CR_{10}R_{23})_nCN$, $(CR_{10}R_{23})_nS(O)_{m'}NR_{13}R_{14}$, $(CR_{10}R_{230})_nC(Z)R_{11}$, $(CR_{10}R_{23})_nOC(Z)R_{11}$, $(CR_{10}R_{23})_nC(Z)OR_{11}$, $(CR_{10}R_{23})_nC(Z)NR_{13}R_{14}$, $(CR_{10}R_{23})_nC(Z)NR_{11}OR_9$, $(CR_{10}R_{23})_nNR_{10}C(Z)R_{11}$, $(CR_{10}R_{23})_nNR_{10}C(Z)NR_{13}R_{14}$, $(CR_{10}R_{23})_nN(OR_6)C(Z)NR_{13}R_{14}$, $(CR_{10}R_{23})_nN(OR_6)C(Z)R_{11}$, $(CR_{10}R_{23})_nC(=NOR_6)R_{11}$, $(CR_{10}R_{23})_nNR_{10}C(=NR_{19})NR_{13}R_{14}$, $(CR_{10}R_{23})_nOC(Z)NR_{13}R_{14}$, $(CR_{10}R_{23})_nNR_{10}C(Z)NR_{13}R_{14}$, $(CR_{10}R_{23})_nNR_{10}C(Z)OR_{10}$, 5-$(R_{18})$-1,2,4-oxadizaol-3-yl or 4-$(R_{12})$-5-$(R_{18}R_{19})$-4,5-dihydro-1,2,4-oxadizaol-3-yl; wherein the cycloalkyl, cycloalkyl alkyl, aryl, arylalkyl, heteroaryl, heteroaryl alkyl, heterocyclic and heterocyclic alkyl groups may be optionally substituted;

$R_3$ is heterocyclyl, heterocyclyl$C_{1-10}$ alkyl or $R_8$;

$R_5$ is hydrogen, $C_{1-4}$ alkyl, $C_{2-4}$ alkenyl, $C_{2-4}$ alkynyl or $NR_7R_{17}$, excluding the moieties $SR_5$ being $SNR_7R_{17}$ and $SOR_5$ being SOH;

$R_6$ is hydrogen, a pharmaceutically acceptable cation, $C_{1-10}$ alkyl, $C_{3-7}$ cycloalkyl, aryl, aryl$C_{1-4}$ alkyl, heteroaryl, heteroaryl$C_{1-4}$ alkyl, heterocyclic, aroyl, or $C_{1-10}$ alkanoyl;

$R_7$ and $R_{17}$ is each independently selected from hydrogen or $C_{1-4}$ alkyl or $R_7$ and $R_{17}$ together with the nitrogen to which they are attached form a heterocyclic ring of 5 to 7 members which ring optionally contains an additional heteroatom selected from oxygen, sulfur or $NR_{15}$;

$R_8$ is $C_{1-10}$ alkyl, halo-substituted $C_{1-10}$ alkyl, $C_{2-10}$ alkenyl, $C_{2-10}$ alkynyl, $C_{3-7}$ cycloalkyl, $C_{5-7}$ cycloalkenyl, aryl, aryl$C_{1-10}$ alkyl, heteroaryl, heteroaryl$C_{1-10}$ alkyl, $CR_{10}R_{20})_nOR_{11}$, $(CR_{10}R_{20})_nS(O)_mR_{18}$, $(CR_{10}R_{20})_nNHS(O)_2R_{18}$, $(C_{10}R_{20})_nNR_{13}R_{14}$; wherein the aryl, arylalkyl, heteroaryl, heteroaryl alkyl containing moieties may be optionally substituted;

$R_9$ is hydrogen, $C(Z)R_{11}$ or optionally substituted $C_{1-10}$ alkyl, $S(O)_2R_{18}$, optionally substituted aryl or optionally substituted aryl-$C_{1-4}$ alkyl;

$R_{10}$ and $R_{20}$ is each independently selected from hydrogen or $C_{1-4}$ alkyl;

$R_{11}$ is hydrogen, $C_{1-10}$ alkyl, $C_{3-7}$ cycloalkyl, heterocyclyl, heterocyclyl $C_{1-10}$alkyl, aryl, aryl$C_{1-10}$ alkyl, heteroaryl or heteroaryl$C_{1-10}$ alkyl;

$R_{12}$ is hydrogen or $R_{16}$;

$R_{13}$ and $R_{14}$ is each independently selected from hydrogen or optionally substituted $C_{1-4}$ alkyl, optionally substituted aryl or optionally substituted aryl-$C_{1-4}$ alkyl, or together with the nitrogen which they are attached form a heterocyclic ring of 5 to 7 members which ring optionally contains an additional heteroatom selected from oxygen, sulfur or $NR_9$;

$R_{15}$ is hydrogen, $C_{1-4}$ alkyl or $C(Z)$—$C_{1-4}$ alkyl;

$R_{16}$ is $C_{1-4}$ alkyl, halo-substituted-$C_{1-4}$ alkyl, or $C_{3-7}$ cycloalkyl;

$R_{18}$ is $C_{1-10}$ alkyl, $C_{3-7}$ cycloalkyl, heterocyclyl, aryl, aryl$C_{1-10}$ alkyl, heterocyclyl, heterocyclyl-$C_{1-10}$alkyl, heteroaryl or heteroarylalkyl;

$R_{19}$ is hydrogen, cyano, $C_{1-4}$ alkyl, $C_{3-7}$ cycloalkyl or aryl;

$R_{23}$ is hydrogen, $C_{1-6}$ alkyl, $C_{3-7}$ cycloalkyl, aryl, aryl$C_{1-4}$ alkyl, heteroaryl, heteroaryl$C_{1-4}$alkyl, heterocyclyl, or heterocyclyl$C_{1-4}$ alkyl moiety, all of which may be optionally substituted;

Z is oxygen or sulfur;

or a pharmaceutically acceptable salt thereof.

In Formula (II), suitable $R_1$, $R_2$, and $R_4$ variables, etc. for use in Formula (II) compounds are the same as those indicated above for Formula (I) compounds and are defined therein. As will be noted the difference between Formula (I) and Formula (II) compounds lay in the saturation of the core ring system.

Exemplified compounds of Formula (II) include:

4-[1-(4-Fluorophenyl)-4,5-dihydro-3-phenyl-1H-pyrazol-5-yl]pyridine

4-[1-(4-Fluorophenyl)-4,5-dihydro-3-[4-(methylthio)phenyl]-1H-pyrazol-5-yl]pyridine Synthetic Methods The compounds of Formula (I) and (II) may be obtained by applying synthetic procedures, some of which are illustrated in Schemes I and II below. The synthesis provided for in these Schemes is applicable for producing compounds of Formula (I) and (II) having a variety of different $R_1$, $R_2$, and $R_4$ groups which are reacted, employing optional substituents which are suitably protected, to achieve compatibility with the reactions outlined herein. Subsequent deprotection, in those cases, then affords compounds of the nature generally disclosed. Once the pyrazole or pyrazoline nucleus has been established, further compounds of Formula (I) or (II) may be prepared by applying standard techniques for functional group interconversion, well known in the art.

For instance: $C(O)NR_{13}R_{14}$ from $CO_2CH_3$ by heating with or without catalytic metal cyanide, e.g. NaCN, and $HNR_{13}R_{14}$ in $CH_3OH$; $OC(O)R_3$ from OH with e.g., $ClC(O)R_3$ in pyridine; $NR_{10}$—$C(S)NR_{13}R_{14}$ from $NHR_{10}$ with an alkylisothiocyante or thiocyanic acid; $NR_6C(O)OR_6$ from $NHR_6$ with the alkyl chloroformate; $NR_{10}C(O)NR_{13}R_{14}$ from $NHR_{10}$ by treatment with an isocyanate, e.g. HN=C=O or $R_{10}N$=C=O; —$NR_{10}$—$C(O)R_8$ from $NHR_{10}$ by treatment with Cl—$C(O)R_3$ in pyridine; $C(=NR_{10})NR_{13}R_{14}$ from $C(NR_{13}R_{14})SR_3$ with $H_3NR_3^+$ $OAc^-$ by heating in alcohol; $C(NR_{13}R_{14})SR_3$ from $C(S)NR_{13}R_{14}$ with $R_6$—I in an inert solvent, e.g. acetone; $C(S)NR_{13}R_{14}$ (where $R_{13}$ or $R_{14}$ is not hydrogen) from $C(S)NH_2$ with $HNR_{13}R_{14}$—$C(=NCN)$—$NR_{13}R_{14}$ from $C(=NR_{13}R_{14})$—$SR_3$ with $NH_2CN$ by heating in anhydrous alcohol, alternatively from $C(=NH)$—$NR_{13}R_{14}$ by treatment with BrCN and NaOEt in EtOH; $NR_{10}$—$C(=NCN)$ $SR_8$ from —$NHR_{10}$ by treatment with $(R_8S)_2C$=NCN; $NR_{10}SO_2R_3$ from $NHR_{10}$ by treatment with $ClSO_2R_3$ by heating in pyridine; $NR_{10}C(S)R_3$ from $NR_{10}C(O)R_8$ by treatment with Lawesson's reagent [2,4-bis(4-methoxyphenyl)-1,3,2,4-dithiadiphosphetane-2,4-disulfide]; $NR_{10}SO_2CF_3$ from $NHR_6$ with triflic anhydride and base wherein $R_3$, $R_6$, $R_{10}$, $R_{13}$ and $R_{14}$ are as defined in Formula (I) herein.

Compounds of Formula (I) are pyrazole derivatives which may be readily prepared using procedures well known to those of skill in the art and may be prepared by analogous methods to those indicated herein below.

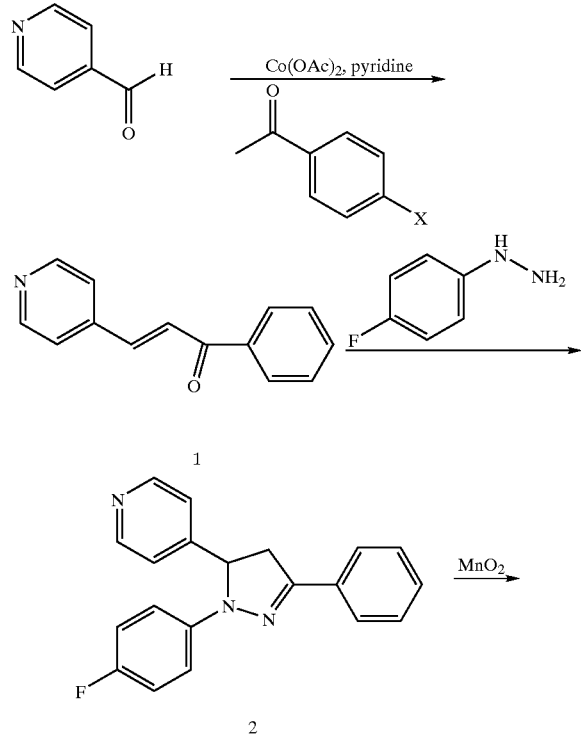

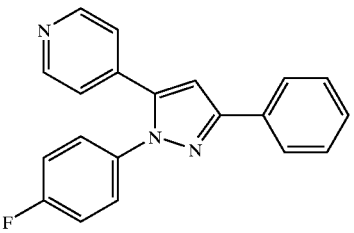

Scheme I illustrates a regioselective synthetic approach to isomerically pure pyrazoles using $Co(OAc)_2$ as the catalyst to effect enone formation. Alternative synthetic methods for the synthesis of compound 1-Scheme 1 include preparation of vinyl organostannane or zirconium reagent from the acetylene and coupling with a suitably functionalized hetereocycle (for example, 4-bromopyridine) using a Pd catalyst. A variety of additional methodologies are available which insure that a wide variety of substitution can be tolerated in compound 1. Similarly, many substituted aryl hydrazines are commercially available or can be readily prepared using standard literature procedures. The pyrazoline, 2, is readily oxidized to 3 with $MnO_2$, but other oxidizing agents may also be used, such as DDQ. The pyrazoline 2 compounds are illustrative of compounds of Formula (II) herein. While the illustration in Scheme I is for the preparation of a particular compound of Formula (I and II) (i.e., Scheme I, $R_1$=pyridyl, $R_4$=4-fluorophenyl, $R_2$=phenyl), generalization of the synthesis to groups claimed as $R_1$, $R_2$, and $R_4$ herein can be achieved by employing the appropriate starting materials.

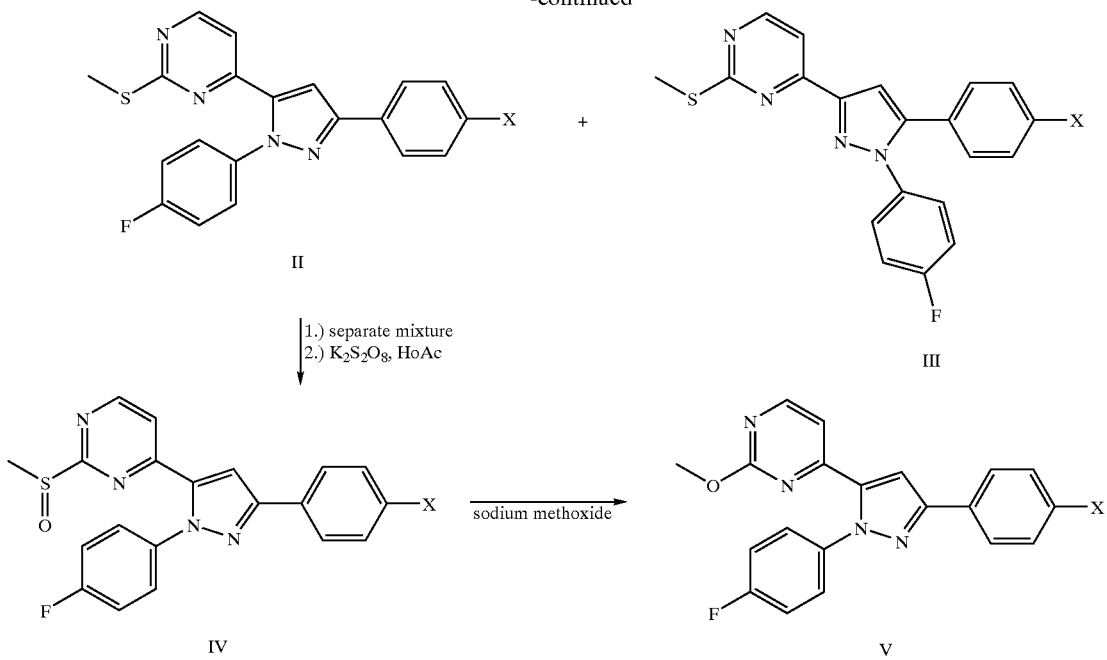

Scheme II illustrates an alternative synthesis of pyrazoles which in many cases will give regioisomeric mixtures of II and III. However, by careful adjustment of the conditions it may be possible to alter this ratio to favor the desired product II. Oxidation of II to the sulfoxide or sulfone activates the heterocyclic ring to nucleophilic substitution. Acceptable nucleophiles are alcohols (compound V) phenols, anilines and amines. The nucleophilic substitution occurs under both acidic and neutral conditions in a wide range of solvents (ether, THF, DMF, toluene, glyme, etc.), but is preferably conducted using the alkali metal salt of the nucleophile.

Suitable protecting groups for use in the present invention, are well known in the art and described in many references, for instance, Protecting Groups in Organic Synthesis, Greene T W, Wiley-Interscience, New York, 1981.

Pharmaceutically acid addition salts of compounds of formula (I) may be obtained in known manner, for example by treatment thereof with an appropriate amount of acid in the presence of a suitable solvent.

Another aspect of the present invention is a process for producing a compound of Formula (I), which process comprises cyclizing a compound of the formula:

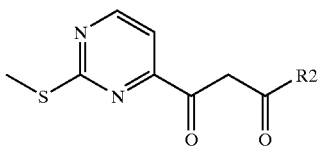

wherein $R_2$ is an optionally substituted phenyl, as defined according to formula (I); with a compound of the formula: $R_4NHNH_2$, wherein $R_4$ is as defined for Formula (I), to yield a compound of Formula (I), or if necessary, converting a precursor of $R_1$, $R_2$ and $R_4$ to a group $R_1$, $R_2$ and $R_4$.

Another aspect of the present invention is a process for producing a compound of Formula (I), wherein $R_1$ is an optionally substituted pyridyl, which process comprises cyclizing a compound of the formula:

wherein $R_2$ is an optionally substituted phenyl, as defined according to formula (I); with a compound of the formula: $R_4NHNH_2$, wherein $R_4$ is as defined for Formula (I), to yield a compound of Formula (I), or if necessary, converting a precursor of $R_1$, $R_2$ and $R_4$ to a group $R_1$, $R_2$ and $R_4$.

The invention will now be described by reference to the following examples which are merely illustrative and are not to be construed as a limitation of the scope of the present invention.

SYNTHETIC EXAMPLES

Example 1

Phenyl-1-(4-pyridyl)prop-1-en-3-one

Pyridine (0.6 g, 7.5 mmol) and Cobalt (ii) acetate (1.3 g, 7.5 mmol) were dissolved in DMF to produce a blue solution of the complex to which was added 4-pyridine carboxaldehyde (5 g, 46.7 mmol) and acetophenone (6.2 g, 51.4 mmol). The resulting mixture was stirred for 18 hours at 90° C. Most of the DMF was evaporated in vacuo and the residue was purified by flash chromatography (silica gel) with 30% EtoAc/Hexane to afford the titled compound, white solid (5 g). ESP+ (Mass Spec) m/z 210 (MH+).

Example 2

1-(4-Fluorophenyl)-3-phenyl-5-(4-pyridyl)-1,2-pyrazoline

Phenyl-1-(4-pyridyl)prop-1-en-3-one (4 g, 19.1 mmol) and 4-fluorophenyl hydrazine hydrochloride salt (4.7 g, 28.7 mmol) were dissolved in ethanol. Sodium acetate (2.4 g, 28.7 mmol) was added. The resulting mixture was stirred for 18 hours at 75° C. Most of the ethanol were evaporated in vacuo. The residue was extracted with EtoAc, washed the organic layer with brine, dried with $Na_2SO_4$ and concentrated under reduced pressure to yield crude eneamine as a brownish solid. (6 g). ESP+ (Mass Spec) m/z 318 (MH+). The eneamine (4.5 g, 14.2 mmol) was dissolved in ethanol and 3N HCl slowly added. The resulting mixture was stirred for 18 hours at 75° C., cooled, poured into water, filtered and the white solid air dried. Recrystallized from EtoAc/Hexane (2:10) to afford the titled compound (4.5 g) ESP+ (Mass Spec) m/z 317 (MH+).

Example 3

1-(4-Fluorophenyl)-3-phenyl-5-(4-pyridyl)pyrazole 1-(4-Fluorophenyl)-3-phenyl-5-(4-pyridyl)-1,2-pyrazoline (0.5 g, 1.57 mmol) and Manganase (iv) oxide (0.16 g, 1.88 mmol) were dissolved in benzene. The resulting mixture was stirred for 18 hours at 25° C., filtered through celite, and concentrated under reduced pressure. The residue was purified by flash chromatography (silica gel) with 40% EtoAc/Hexane to afford the titled compound, yellow solid (5 g). ESP+ (Mass Spec) m/z 316 (MH+).

Example 4

1-(4-Fluorophenyl)-3-phenyl-4-bromo-5-(4-pyridyl) pyrazole 1-(4-Fluorophenyl)-3-phenyl-5-(4-pyridyl)-1,2-pyrazoline (0.6 g, 1.89 mmol) was dissolved in 5% aqueous bromine. The resulting mixture was stirred for 18 hours at 25° C. The residue was neutralized with aqueous NaOH, extracted with EtOAc, washed with brine, dried over $Na_2SO_4$ and concentrated to produce an off white solid. Recrystallization from EtOAc/Hexane (2:10) afforded the titled compound, (17 mg). ESP+ (Mass Spec) m/z 395 (MH+).

Example 5

(E)-1-(4-methylthiophenyl)-3-(4-pyridyl)-2-propenone

To a mixture of cobalt (ii) acetate (4 g, 23.0 mmol) in pyridine was added 4-pyridine carboxaldehyde (5 g, 46.7 mmol) and 4-(methylthio) acetophenone (8 g, 48.12 mmol). The resulting mixture was heated for 18 hours at 90° C. Following concentration under reduced pressure, the residue was purified by flash chromatography (silica gel) with 30% EtoAc/Hexane to afford the titled compound, white solid (3 g). ESP+ (Mass Spec) m/z 256 (MH+).

Example 6

1-(4-Fluorophenyl)-3-4-(thiomethylphenyl)-5-(4-pyridyl)-1,2-pyrazoline (E)-1-(4-methylthiophenyl)-3-(4-pyridyl)-2-propenone (3 g, 11.7 mmol) and 4-fluorophenylhydrazine hydrochloride salt (3 g, 18.5 mmol) were dissolved in ethanol to which sodium acetate (1.5 g, 18.5 mmol) was added. The resulting mixture was stirred for 18 hours at 75° C. after which the bulk of the ethanol was removed under reduced pressure. The residue was extracted with EtOAc, the organic layer was washed with brine, dried with $Na_2SO_4$ and concentrated to yield the crude eneamine as a brownish solid (3 g). ESP+ (Mass Spec) m/z 363 (MH+). eneamine (6 g). ESP+ (Mass Spec) m/z 318 (MH+).

The eneamine (3 g, 8.3 mmol) was dissolved in ethanol and 3N HCl added slowly. The resulting mixture was stirred for 18 hours at 75° C., cooled, and poured into water. The resulting precipitate was filtered and the white solid air dried. Recrystallization from EtoAc/Hexane (2:10) afforded the titled compound (4.5 g) ESP+ (Mass Spec) m/z 363 (MH+).

Example 7

1-(4-Fluorophenyl)-3-4-thiomethylphenyl)-5-(4-pyridyl) pyrazole 1-(4-Fluorophenyl)-3-4-thiomethylphenyl)-5-(4-pyridyl)-1,2-pyrazoline (2.1 g, 5.8 mmol) and manganase (iv)oxide (0.66 g, 7.6 mmol) were dissolved in benzene. The resulting mixture was stirred for 18 hours at 25° C., filtered through celite, and concentrated under reduced pressure. The residue was purified by flash chromatography (silica gel) with 40% EtoAc/Hexane to afford the titled compound, brownished solid (125 mg). ESP+ (Mass Spec) m/z 362 (MH+).

Example 8

1-(4-Fluorophenyl)-3-(4-methylsulfonylphenyl)-5(4-pyridyl)pyrazole 1-(4-Fluorophenyl)-3-(4-thiomethylphenyl)-5-(4-pyridyl) pyrazole was dissolved in THF cooled to −10° C. and oxone (3.2 g, 5.26 mmol) in water (15 ml) was added dropwise (T<5° C.). The resulting mixture was warmed to 20° C. over 50 min. and then poured into a vigorously stirred mixture of 10% aqeuous NaOH (160 ml), extracted with EtoAc, dried ($Na_2SO_4$), and concentrated to a brownished solid. Recrystallization from EtoAc/Hexane(1:10) afforded the titled compound (50 mg). ESP+ (Mass Spec) m/z 394 (MH+).

Methods of Treatment

The compounds of Formula (I) or (II) or a pharmaceutically acceptable salt thereof can be used in the manufacture of a medicament for the prophylactic or therapeutic treatment of any disease state in a human, or other mammal, which is exacerbated or caused by excessive or unregulated cytokine production by such mammal's cell, such as but not limited to monocytes and/or macrophages.

As used herein, unless specifically indicated, compounds of Formula (I) also include compounds of Formula (II).

Compounds of Formula (I) are capable of inhibiting proinflammatory cytokines, such as IL-1, IL-6, IL-8 and TNF and are therefore of use in therapy. IL-1, IL-6, IL-8 and TNF affect a wide variety of cells and tissues and these cytokines, as well as other leukocyte-derived cytokines, are important and critical inflammatory mediators of a wide variety of disease states and conditions. The inhibition of these pro-inflammatory cytokines is of benefit in controlling, reducing and alleviating many of these disease states.

Accordingly, the present invention provides a method of treating a cytokine-mediated disease which comprises administering an effective cytokine-interfering amount of a compound of Formula (I) or a pharmaceutically acceptable salt thereof.

In particular, compounds of Formula (I) or a pharmaceutically acceptable salt thereof are of use in the prophylaxis or therapy of any disease state in a human, or other mammal, which is exacerbated by or caused by excessive or unregulated IL-1, IL-8 or TNF production by such mammal's cell, such as, but not limited to, monocytes and/or macrophages.

Accordingly, in another aspect, this invention relates to a method of inhibiting the production of IL-1 in a mammal in need thereof which comprises administering to said mammal an effective amount of a compound of Formula (I) or a pharmaceutically acceptable salt thereof.

There are many disease states in which excessive or unregulated IL-1 production is implicated in exacerbating and/or causing the disease. These include rheumatoid arthritis, osteoarthritis, stroke, endotoxemia and/or toxic shock syndrome, other acute or chronic inflammatory disease states such as the inflammatory reaction induced by endotoxin or inflammatory bowel disease, tuberculosis, atherosclerosis, muscle degeneration, multiple sclerosis, cachexia, bone resorption, psoriatic arthritis, Reiter's syndrome, rheumatoid arthritis, gout, traumatic arthritis, rubella arthritis and acute synovitis. Recent evidence also links IL-1 activity to diabetes, pancreatic β cells and Alzheimer's disease.

In a further aspect, this invention relates to a method of inhibiting the production of TNF in a mammal in need thereof which comprises administering to said mammal an effective amount of a compound of Formula (I) or a pharmaceutically acceptable salt thereof.

Excessive or unregulated TNF production has been implicated in mediating or exacerbating a number of diseases including rheumatoid arthritis, rheumatoid spondylitis, osteoarthritis, gouty arthritis and other arthritic conditions, sepsis, septic shock endotoxic shock, gram negative sepsis, toxic shock syndrome, adult respiratory distress syndrome, stroke, cerebral malaria, chronic pulmonary inflammatory disease, silicosis, pulmonary sarcoisosis, bone resorption diseases, such as osteoporosis, reperfusion injury, graft vs. host reaction, allograft rejections, fever and myalgias due to infection, such as influenza, cachexia secondary to infection or malignancy, cachexia secondary to acquired immune deficiency syndrome (AIDS), AIDS, ARC (AIDS related complex), keloid formation, scar tissue formation, inflammatory bowel disease, Crohn's disease, ulcerative colitis and pyresis.

Compounds of Formula (I) are also useful in the treatment of viral infections, where such viruses are sensitive to upregulation by TNF or will elicit TNF production in vivo. The viruses contemplated for treatment herein are those that produce TNF as a result of infection, or those which are sensitive to inhibition, such as by decreased replication, directly or indirectly, by the TNF inhibiting-compounds of Formula (1). Such viruses include, but are not limited to HIV-1, HIV-2 and HIV-3, Cytomegalovirus (CMV), Influenza, adenovirus and the Herpes group of viruses, such as but not limited to, *Herpes Zoster* and *Herpes Simplex*. Accordingly, in a further aspect, this invention relates to a method of treating a mammal afflicted with a human immunodeficiency virus (HIV) which comprises administering to such mammal an effective TNF inhibiting amount of a compound of Formula (I) or a pharmaceutically acceptable salt thereof.

Compounds of Formula (I) may also be used in association with the veterinary treatment of mammals, other than in humans, in need of inhibition of TNF production. TNF mediated diseases for treatment, therapeutically or prophylactically, in animals include disease states such as those noted above, but in particular viral infections. Examples of such viruses include, but are not limited to, lentivirus infections such as, equine infectious anaemia virus, caprine arthritis virus, visna virus, or maedi virus or retrovirus infections, such as but not limited to feline immunodeficiency virus (FIV), bovine immunodeficiency virus, or canine immunodeficiency virus or other retroviral infections.

The compounds of Formula (I) may also be used topically in the treatment or prophylaxis of topical disease states mediated by or exacerbated by excessive cytokine production, such as by IL-1 or TNF respectively, such as inflamed joints, eczema, contact dermatitis, psoriasis and other inflammatory skin conditions such as sunburn; inflammatory eye conditions including conjunctivitis; pyresis, pain and other conditions associated with inflammation.

Compounds of Formula (I) have also been shown to inhibit the production of IL-8 (Interleukin-8, NAP). Accordingly, in a further aspect, this invention relates to a method of inhibiting the production of IL-8 in a mammal in need thereof which comprises administering to said mammal an effective amount of a compound of Formula (I) or a pharmaceutically acceptable salt thereof.

There are many disease states in which excessive or unregulated IL-8 production is implicated in exacerbating and/or causing the disease. These diseases are characterized by massive neutrophil infiltration such as, psoriasis, inflammatory bowel disease, asthma, cardiac and renal reperfusion injury, adult respiratory distress syndrome, thrombosis and glomerulonephritis. All of these diseases are associated with increased IL-8 production which is responsible for the chemotaxis of neutrophils into the inflammatory site. In contrast to other inflammatory cytokines (IL-1, TNF, and IL-6), IL-8 has the unique property of promoting neutrophil chemotaxis and activation. Therefore, the inhibition of IL-8 production would lead to a direct reduction in the neutrophil infiltration.

The compounds of Formula (I) are administered in an amount sufficient to inhibit cytokine, in particular IL-1, IL-6, IL-8 or TNF, production such that it is regulated down to normal levels, or in some case to subnormal levels, so as to ameliorate or prevent the disease state. Abnormal levels of IL-1, IL-6, IL-8 or TNF, for instance in the context of the present invention, constitute: (i) levels of free (not cell bound) IL-1, IL-6, IL-8 or TNF greater than or equal to picogram per ml; (ii) any cell associated IL-1, IL-6, IL-8 or TNF; or (iii) the presence of IL-1, IL-6, IL-8 or TNF mRNA above basal levels in cells or tissues in which IL-1, IL-6, IL-8 or TNF, respectively, is produced.

The discovery that the compounds of Formula (I) are inhibitors of cytokines, specifically IL-1, IL-6, IL-8 and TNF is based upon the effects of the compounds of Formulas (I) on the production of the IL-1, IL-8 and TNF in in vitro assays which are described herein.

As used herein, the term "inhibiting the production of IL-1 (IL-6, IL-8 or TNF)" refers to:

a) a decrease of excessive in vivo levels of the cytokine (IL-1, IL-6, IL-8 or TNF) in a human to normal or sub-normal levels by inhibition of the in vivo release of the cytokine by all cells, including but not limited to monocytes or macrophages;

b) a down regulation, at the genomic level, of excessive in vivo levels of the cytokine (IL-1, IL-6, IL-8 or TNF) in a human to normal or sub-normal levels;

c) a down regulation, by inhibition of the direct synthesis of the cytokine (IL-1, IL-6, IL-8 or TNF) as a postranslational event; or d) a down regulation, at the translational level, of excessive in vivo levels of the cytokine (IL-1, IL-6, IL-8 or TNF) in a human to normal or sub-normal levels.

As used herein, the term "TNF mediated disease or disease state" refers to any and all disease states in which TNF plays a role, either by production of TNF itself, or by TNF causing another monokine to be released, such as but not limited to IL-1, IL-6 or IL-8. A disease state in which, for instance, IL-1 is a major component, and whose production or action, is exacerbated or secreted in response to TNF, would therefore be considered a disease stated mediated by TNF.

As used herein, the term "cytokine" refers to any secreted polypeptide that affects the functions of cells and is a molecule which modulates interactions between cells in the immune, inflammatory or hematopoietic response. A cytokine includes, but is not limited to, monokines and lymphokines, regardless of which cells produce them. For instance, a monokine is generally referred to as being produced and secreted by a mononuclear cell, such as a macrophage and/or monocyte. Many other cells however also produce monokines, such as natural killer cells, fibroblasts, basophils, neutrophils, endothelial cells, brain astrocytes, bone marrow stromal cells, epideral keratinocytes and B-lymphocytes. Lymphokines are generally referred to as being produced by lymphocyte cells. Examples of cytokines include, but are not limited to, Interleukin-1 (IL-1), Interleukin-6 (IL-6), Interleukin-8 (IL-8), Tumor Necrosis Factor-alpha (TNF-α) and Tumor Necrosis Factor beta (TNF-β).

As used herein, the term "cytokine interfering" or "cytokine suppressive amount" refers to an effective amount of a compound of Formula (I) which will cause a decrease in the in vivo levels of the cytokine to normal or sub-normal levels, when given to a patient for the prophylaxis or treatment of a disease state which is exacerbated by, or caused by, excessive or unregulated cytokine production.

As used herein, the cytokine referred to in the phrase "inhibition of a cytokine, for use in the treatment of a HIV-infected human" is a cytokine which is implicated in (a) the initiation and/or maintenance of T cell activation and/or activated T cell-mediated mediated HIV gene expression and/or replication and/or (b) any cytokine-mediated disease associated problem such as cachexia or muscle degeneration.

As TNF-β (also known as lymphotoxin) has close structural homology with TNF-α (also known as cachectin) and since each induces similar biologic responses and binds to the same cellular receptor, both TNF-α and TNF-β are inhibited by the compounds of the present invention and thus are herein referred to collectively as "TNF" unless specifically delineated otherwise.

A new member of the MAP kinase family, alternatively termed CSBP, p38, or RK, has been identified independently by several laboratories recently [See Lee et al., Nature, Vol. 300 n(72), 739–746 (1994)]. Activation of this novel protein kinase via dual phosphorylation has been observed in different cell systems upon stimulation by a wide spectrum of stimuli, such as physicochemical stress and treatment with lipopolysaccharide or proinflammatory cytokines such as interleukin-1 and tumor necrosis factor. The cytokine biosynthesis inhibitors, of the present invention, compounds of Formula (I), have been determined to be potent and selective inhibitors of CSBP/p38/RK kinase activity. These inhibitors are of aid in determining the signaling pathways involvement in inflammatory responses. In particular, for the first time a definitive signal transduction pathway can be prescribed to the action of lipopolysaccharide in cytokine production in macrophages. In addition to those diseases already noted, treatment of stroke, neurotrauma, cardiac and renal reperfusion injury, chronic renal failure, congestive heart failure, cancer, thrombosis, glomerulonephritis, diabetes and pancreatic β cells, multiple sclerosis, muscle degeneration eczema, psoriasis, sunburn, and conjunctivitis are also included.

The cytokine inhibitors were subsequently tested in a number of animal models for anti-inflammatory activity. Model systems were chosen that were relatively insensitive to cyclooxygenase inhibitors in order to reveal the unique activities of cytokine suppressive agents. The inhibitors exhibited significant activity in many such in vivo studies. Most notable are its effectiveness in the collagen-induced arthritis model and inhibition of TNF production in the endotoxic shock model. In the latter study, the reduction in plasma level of TNF correlated with survival and protection from endotoxic shock related mortality. Also of great importance are the compounds effectiveness in inhibiting bone resorption in a rat fetal long bone organ culture system. Griswold et al., (1988) *Arthritis Rheum.* 31:1406–1412; Badger, et al., (1989) *Circ. Shock* 27, 51–61; Votta et al., (1994)*in vitro. Bone* 15, 533–538; Lee et al., (1993), B *Ann. N. Y. Acad. Sci.* 696, 149–170.

Another aspect of the present invention is to the novel use of these CSBP/cytokine inhibitors for the treatment of chronic inflammatory or proliferative or angiogenic diseases which are caused by excessive, or inappropriate angiogenesis.

Chronic diseases which have an inappropriate angiogenic component are various ocular neovasularizations, such as diabetic retinopathy and macular degeneration. Other chronic diseases which have an excessive or increased proliferation of vasculature are tumor growth and metastasis, atherosclerosis, and certain arthritic conditions. Therefore cytokine inhibitors will be of utility in the blocking of the angiogenic component of these disease states.

The term "excessive or increased proliferation of vasculature inappropriate angiogenesis" as used herein includes, but is not limited to, diseases which are characterized by hemangiomas and ocular diseases.

The term "inappropriate angiogenesis" as used herein includes, but is not limited to, diseases which are characterized by vesicle proliferation with accompanying tissue proliferation, such as occurs in cancer, metastasis, arthritis and atherosclerosis.

In order to use a compound of Formula (I) or a pharmaceutically acceptable salt thereof in therapy, it will normally be Formulated into a pharmaceutical composition in accordance with standard pharmaceutical practice. This invention, therefore, also relates to a pharmaceutical composition comprising an effective, non-toxic amount of a compound of Formula (I) and a pharmaceutically acceptable carrier or diluent.

Compounds of Formula (I), pharmaceutically acceptable salts thereof and pharmaceutical compositions incorporating such may conveniently be administered by any of the routes conventionally used for drug administration, for instance, orally, topically, parenterally or by inhalation. The compounds of Formula (I) may be administered in conventional dosage forms prepared by combining a compound of Formula (I) with standard pharmaceutical carriers according to conventional procedures. The compounds of Formula (I) may also be administered in conventional dosages in combination with a known, second therapeutically active compound. These procedures may involve mixing, granulating and compressing or dissolving the ingredients as appropriate to the desired preparation. It will be appreciated that the form and character of the pharmaceutically acceptable character or diluent is dictated by the amount of active ingredient with which it is to be combined, the route of administration and other well-known variables. The carrier(s) must be "acceptable" in the sense of being compatible with the other ingredients of the Formulation and not deleterious to the recipient thereof.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as glyceryl mono-stearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg. to about 1 g. When a liquid carrier is used, the preparation will be in the form of a syrup, emulsion, soft gelatin capsule, sterile injectable liquid such as an ampule or nonaqueous liquid suspension.

Compounds of Formula (I) may be administered topically, that is by non-systemic administration. This includes the application of a compound of Formula (I) externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as liniments, lotions, creams, ointments or pastes, and drops suitable for administration to the eye, ear or nose. The active ingredient may comprise, for topical administration, from 0.001% to 10% w/w, for instance from 1% to 2% by weight of the Formulation. It may however comprise as much as 10% w/w but preferably will comprise less than 5% w/w, more preferably from 0.1% to 1% w/w of the Formulation Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid Formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin. glycerol, beeswax, a metallic soap; a mucilage; an oil of natural origin such as almond, corn, arachis, castor or olive oil; wool fat or its derivatives or a fatty acid such as steric or oleic acid together with an alcohol such as propylene glycol or a macrogel. The Formulation may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as silicaceous silicas, and other ingredients such as lanolin, may also be included.

Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified by filtration, transferred to a suitable container which is then sealed and sterilized by autoclaving or maintaining at 98–100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Compounds of formula (I) may be administered parenterally, that is by intravenous, intramuscular, subcutaneous intranasal, intrarectal, intravaginal or intraperitoneal administration. The subcutaneous and intramuscular forms of parenteral administration are generally preferred. Appropriate dosage forms for such administration may be prepared by conventional techniques. Compounds of Formula (I) may also be administered by inhalation, that is by intranasal and oral inhalation administration. Appropriate dosage forms for such administration, such as an aerosol Formulation or a metered dose inhaler, may be prepared by conventional techniques.

For all methods of use disclosed herein for the compounds of Formula (I), the daily oral dosage regimen will preferably be from about 0.1 to about 80 mg/kg of total body weight, preferably from about 0.2 to 30 mg/kg, more preferably from about 0.5 mg to 15 mg. The daily parenteral dosage regimen about 0.1 to about 80 mg/kg of total body weight, preferably from about 0.2 to about 30 mg/kg, and more preferably from about 0.5 mg to 15 mg/kg. The daily topical dosage regimen will preferably be from 0.1 mg to 150 mg, administered one to four, preferably two or three times daily. The daily inhalation dosage regimen will preferably be from about 0.01 mg/kg to about 1 mg/kg per day. It will also be recognized by one of skill in the art that the optimal quantity and spacing of individual dosages of a compound of Formula (I) or a pharmaceutically acceptable salt thereof will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses of a compound of Formula (I) or a pharmaceutically acceptable salt thereof given per day for a defined number of days, can be ascertained by those skilled in the art using conventional course of treatment determination tests.

The invention will now be described by reference to the following biological examples which are merely illustrative and are not to be construed as a limitation of the scope of the present invention.

BIOLOGICAL EXAMPLES

The cytokine-inhibiting effects of compounds of the present invention were determined by the following in vitro assays:

Interleukin-1 (IL-1), Interleukin-8 (IL-8), and Tumour Necrosis Factor (TNF) assays may be found in a number of publications, in particular suitable assays for use herein are described in Adams et al., U.S. Pat. No. 5,593,992, whose disclosure is incorporated by reference.

In Vivo TNF Assay:

While the above indicated assay in an in vitro assay, the compounds of Formula (I) may also be tested in an in vivo system such as described in:

(1) Griswold et al., *Drugs Under Exp. and Clinical Res.,XIX* (6), 243–48 (1993); or (2) Boehm, et al., *Journal Of Medicinal Chemistry* 39, 3929–3937 (1996) whose disclosures are incorporated by reference herein in their entirety.

LPS-Induced TNFα Production in Mice and Rats

In order to evaluate in vivo inhibition of LPS-induced TNFα production in rodents, both mice and rats are injected with LPS.

Mouse Method

Male Balb/c mice from Charles River Laboratories are pretreated (30 minutes) with compound or vehicle. After the 30 min. pretreat time, the mice are given LPS (lipopolysaccharide from *Esherichia coli* Serotype 055-85, Sigma Chemical Co., St Louis, Mo.) 25 ug/mouse in 25 ul phosphate buffered saline (pH 7.0) intraperitoneally. Two hours later the mice are killed by $CO_2$ inhalation and blood samples are collected by exsanguination into heparinized blood collection tubes and stored on ice. The blood samples are centrifuged and the plasma collected and stored at −20° C. until assayed for TNFα by ELISA.

Rat Method

Male Lewis rats from Charles River Laboratories are pretreated at various times with compound or vehicle. After a determined pretreat time, the rats are given LPS (lipopolysaccharide from *Esherichia coli* Serotype 055-85, Sigma Chemical Co., St Louis, Mo.) 3.0 mg/kg intraperitoneally. The rats are killed by $CO_2$ inhalation and heparinized whole blood is collected from each rat by cardiac puncture 90 minutes after the LPS injection. The blood samples are centrifuged and the plasma collected for analysis by ELISA for TNFα levels.

Elisa Method

TNFα levels were measured using a sandwich ELISA, as described in Olivera et al., Circ. Shock, 37, 301–306, (1992), whose disclosure is incorporated by reference in its entirety herein, using a hamster monoclonal antimurine TNFα (Genzyme, Boston, Mass.) as the capture antibody and a polyclonal rabbit antimurine TNFα (Genzyme) as the second antibody. For detection, a peroxidase-conjugated goat antirabbit antibody (Pierce, Rockford, Ill.) was added, followed by a substrate for peroxidase (1 mg/ml orthophenylenediamine with 1% urea peroxide). TNFα levels in the plasma samples from each animal were calculated from a standard curve generated with recombinant murine TNFα (Genzyme).

LPS-Stimulated Cytokine Production in Human Whole Blood

Assay: Test compound concentrations were prepared at 10×concentrations and LPS prepared at 1 ug/ml (final conc. of 50 ng/ml LPS) and added in 50 uL volumes to 1.5 mL eppendorf tubes. Heparinized human whole blood was obtained from healthy volunteers and was dispensed into eppendorf tubes containing compounds and LPS in 0.4 mL volumes and the tubes incubated at 37 C. Following a 4 hour incubation, the tubes were centrifuged at 5000 rpm for 5 minutes in a TOMY microfuge, plasma was withdrawn and frozen at −80 C.

Cytokine measurement: IL-I and/or TNF were quantified using a standardized ELISA technology. An in-house ELISA kit was used to detect human IL-1 and TNF. Concentrations of IL-1 or TNF were determined from standard curves of the appropriate cytokine and IC50 values for test compound (concentration that inhibited 50% of LPS-stimulated cytokine production) were calculated by linear regression analysis.

CSBP Kinase Assay:

This assay measures the CSBP-catalyzed transfer of $^{32}P$ from [a-$^{32}P$]ATP to threonine residue in an epidermal growth factor receptor (EGFR)-derived peptide (T669) with the following sequence: KRELVEPLTPSGEAPNQALLR (residues 661–681). (See Gallagher et al., "Regulation of Stress Induced Cytokine Production by Pyridinyl Imidazoles: Inhibition of CSPB Kinase", BioOrganic & Medicinal Chemistry, to be published 1996).

Kinase reactions (total volume 30 ul) contain: 25 mM Hepes buffer, pH 7.5; 10 mM $MgCl_2$; 170 uM ATP[(1)]; 10 uM Na ortho vanadate; 0.4 mM T669 peptide; and 20–80 ng of yeast-expressed purified CSBP2 (see Lee et al., *Nature* 300, n(72), 739–746 (December 1994)). Compounds (5 ul from [6×] stock[(2)]) are pre-incubated with the enzyme and peptide for 20 min. on ice prior to starting the reactions with 32 P/MgATP. Reactions are incubated at 30° C. for 10 min. and stopped by adding 10 ul of 0.3 M phosphoric acid. 32P-labeled peptide is separated on phosphocellulose (Wattman, p81) filters by spotting 30 ul reaction mixture. Filters are washed 3 times with 75 mM phosphoric acid followed by 2 washes with $H_2O$, and counted for 32P.

(1) The Km of CSBP for ATP was determined to be 170 uM. Therefore, compounds screened at the Km value of ATP.

(2) Compounds are usually dissolved in DMSO and are diluted in 25 mM HEPES buffer to get final concentration of DMSO of 0.17%.

Representative compounds of Formula (I) and (II), Examples 2, 3, 4, 7 and 8 herein all demonstrated a positive inhibitory activity in this assay having an IC50<50 uM.

Prostoglandin Endoperoxide Synthase-2 (PGHS-2) Assay:

This assay describes a method for determining the inhibitory effects of compounds of Formula (I) on human PGHS-2 protein expression in LPS stimulated human monocytes. A suitable assay for PGHS-2 protein expression may be found in a number of publications, including U.S. Pat. No. 5,593, 992 whose disclosure is incorporated herein by reference.

TNF-α in Traumatic Brain Injury Assay

This assay provides for examination of the expression of tumor necrosis factor mRNA in specific brain regions which follow experimentally induced lateral fluid-percussion traumatic brain injury (TBI) in rats. Since TNF-α is able to induce nerve growth factor (NGF) and stimulate the release of other cytokines from activated astrocytes, this post-traumatic alteration in gene expression of TNF-α plays an important role in both the acute and regenerative response to CNS trauma. A suitable assay may be found in WO 97/35856 whose disclosure is incorporated herein by reference.

CNS Injury Model for IL-β mRNA

This assay characterizes the regional expression of interleukin-1β (IL-1β) mRNA in specific brain regions following experimental lateral fluid-percussion traumatic brain injury (TBI) in rats. Results from these assays indicate that following TBI, the temporal expression of IL-1β mRNA is regionally stimulated in specific brain regions. These regional changes in cytokines, such as IL-1β play a role in the post-traumatic pathologic or regenerative sequelae of brain injury. A suitable assay may be found in WO 97/35856 whose disclosure is incorporated herein by reference.

Angiogenesis Assay:

Described below is an assay for determination of inflammatory angiogenesis which may be used to show that cytokine inhibition will stop the tissue destruction of excessive or inappropriate proliferation of blood vessels.

The murine airpouch granuloma model of chronic inflammation (Kimura et al., 1985, J. Pharmacobio-Dyn., 8:393–400; Colville-Nash et al.,1995, J. Pharm. and Exp. Ther., 274:1463–1472) whose disclosure is incorporated herein by reference in its entirety, is characterized by inflammatory cell influx, fibrous tissue proliferation and intense angiogenesis. It is representative of inflammatory angiogenesis and demonstrates that the angiogenic component can be pharmacologically modulated independently of granuloma growth and size. In addition, angiogenesis can be accurately quantitated by a vascular casting method.

The effect of a compound on vascular density (and dry weight) is measured for 6 days after induction of the granuloma. This time point has previously been determined to be at or near the peak of angiogenesis. A positive control medroxyprogesterone, an angiostatic steroid (Gross et al., 1981, Proc. Natl. Acad. Sci. USA, 78:1176–1180)—whose disclosure is hereby incorporated by reference in its entirety, is utilized.

Methods: Murine Air Pouch Granuloma Model:

Day -1, mice are anesthetized using Aerrane (isoflurane) gas (5%), after which 3 mls of air is injected into the dorsal subcutaneous tissue using a 27 g needle. Mice are allowed to recover.

Day 0, mice are again anesthetized using Aerrane, once anesthetized 0.5 ml of Freunds complete adjuvant with 0.1% v/v croton oil is injected into the air pouch formed on Day-1. The animals also begin their dosing regime (number of days dependent upon study) with the animals typically receiving compound in 0.2 ml N,N, Dimethyl Acetoacetamide(DMA) (Sigma, St. Louis, Mo.)/Cremephor El (Sigma, St. Louis, Mo.)/saline (Oct. 10, 1980) or other appropriate vehicle. The animals are allowed to recover and all subsequent dosing is performed on the animals in the absence of anesthetics.

Days 1–5, Animals are dosed according to schedule.

On Day 6 the animals are again anesthetized using Aerrane after which a vascular cast is made (Kimura et al., 1986, J.Pharmacobio-Dyn, 9:442–446), this involves a 1 ml tail vein i.v. injection of a Carmine Red(10%)(Sigma, St. Louis, Mo.)/gelatin (5%)(Sigma, St. Louis, Mo.) solution. The animals are then sacrificed by lethal dose of anesthesia and chilled at 4 C for 2 hours prior to the removal of the granuloma tissue.

When the granuloma is removed it is weighed and then dried for 3 days at 45 C and reweighed. The dried tissue is then digested in 0.9 ml of a 0.05 M phosphate buffer pH 7.0 containing 12 U/ml$^{-1}$ papain (Sigma, St. Totiis, Mo.) and 0.33 g/L$^{-1}$ N-acetyl-1-Cysteine (Sigma, St. Louis, Mo.) at 57 C for 3 days. After 3 days digestion the carmine red is solubilized by the addition of 0.1 ml 5 mM NaOH. Samples are centrifuged and then filtered using 0.2 um acrodiscs. The carmine content is then determined against a carmine red standard curve (0.5 to 2 mg/ml) generated in extracted tissue from non carmine treated animals and read at 490 nm. Sample and standard values are determined using DeltaSoft Elisa analysis software (Biometallics Inc., Princeton, N.J.). The carmine content is then used to determine the vascular indexes for the various treatments, vascular index being the mg carmine dye/gm dry tissue.

Tissue extracts are made by homogenizing granulomas in 0.5 ml 5 mM KH$_2$PO$_4$/0.1 gm wet tissue. IL-1β levels are determined using a Cytoscreen Immunoassay Kit (catalog # KMC 0012) from BioSource International, Camarillo, Calif. TNF-α levels are determined using the following assay: plates were coated with hamster anti-murine TNF-α antibody (Genzyme, Cambridge, Mass.), for 2 hours at 37° C., washed and blocked with a casein-BSA solution (5 gram/L for each) for 1 hour at 37° C., the samples are added and incubated at 4° C. overnight. Plates are washed, and the secondary antibody, Rabbit Anti-mouse TNF-α (Genzyme), was added for 2 hours at 37° C., the plates were washed, and the tertiary antibody Goat Anti-rabbit peroxidase conjugate (BioSource International, Camarillo, Calif.) is added for 2 hours at 37° C. The plates are then washed, and substrate OPD (Sigma) is added for 20 minutes at room temperature. The reaction is terminated with 25 ul 0.1M NaF per well, the O.D. read at 460 nm. Sample values for both ELISAs are calculated using DeltaSoft ELISA analysis software (Biomettalics Inc., Princeton, N.J.).

All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration, it is believed that one skilled in the are can, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follows.

What is claimed is:

1. A compound of the formula:

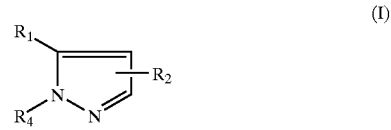

(I)

wherein

R$_1$ is a 4-pyrimidinyl, 4-pyridazinyl, 1,2,4-triazin-5-yl, ring, which ring is optionally substituted independently one to three times with Y, NHR$_a$, optionally substituted C$_{1-4}$ alkyl, halogen, hydroxyl, optionally substituted C$_{1-4}$ alkoxy, optionally substituted C$_{1-4}$ alkylthio, optionally substituted C$_{1-4}$ alkylsulfinyl, CH$_2$OR$_{12}$, amino, mono and di- C$_{1-6}$ alkyl substituted amino, N(R$_{10}$)C(O)R$_b$, N(R$_{10}$)S(O)$_2$R$_d$, or an N-heterocyclyl ring which ring has from 5 to 7 members and optionally contains an additional heteroatom selected from oxygen, sulfur or NR$_{15}$;

Y is X$_1$—R$_a$;

X$_1$ is sulfur or oxygen;

R$_a$ is C$_{1-6}$alkyl, aryl, arylC$_{1-6}$alkyl, heterocyclic, heterocyclylC$_{1-6}$ alkyl, heteroaryl, or heteroarylC$_{1-6}$ alkyl, wherein each of these moieties may be optionally substituted;

R$_b$ is hydrogen, C$_{1-6}$ alkyl, C$_{3-7}$ cycloalkyl, aryl, arylC$_{1-4}$ alkyl, heteroaryl, heteroarylC$_{1-4}$alkyl, heterocyclyl, or heterocyclylC$_{1-4}$ alkyl;

R$_d$ is C$_{1-6}$ alkyl, C$_{3-7}$ cycloalkyl, aryl, arylC$_{1-4}$ alkyl, heteroaryl, heteroarylC$_{1-4}$alkyl, heterocyclyl, or heterocyclylC$_{1-4}$ alkyl;

R$_4$ is phenyl, naphth-1-yl or naphth-2-yl, which is optionally substituted by one to three substituents, each of which is independently selected, and which, for a 4-phenyl, 4-naphth-1-yl, 5-naphth-2-yl or 6-naphth-2-yl substituent, is halogen, cyano, nitro, C(Z)NR$_7$R$_{17}$, C(Z)OR$_{16}$, (CR$_{10}$R$_{20}$)$_v$COR$_{12}$, SR$_5$, S(O)R$_5$, OR$_{12}$halo-substituted-C$_{1-4}$ alkyl, C$_{1-4}$ alkyl, ZC(Z)R$_{12}$, NR$_{10}$C(Z)R$_{16}$, or (CR10R$_{20}$)$_v$NR$_{10}$R$_{20}$ and which, for other positions of substitution, is halogen, cyano, nitro, phenyl, C(Z)NR$_{13}$R$_{14}$, C(Z)OR$_3$, (CR$_{10}$R$_{20}$)$_{m''}$COR$_3$, S(O)$_m$R$_3$, OR$_3$, halo-substituted-C$_{1-4}$ alkyl, C$_{1-10}$ alkyl, ZC(Z)R$_3$, optionally substituted phenyl (CR$_{10}$R$_{20}$)$_{m''}$NR$_{10}$C(Z)R$_3$, NR$_{10}$S(O)$_m$R$_8$, NR$_{10}$S(O)$_m$NR$_7$R$_{17}$, or (CR$_{10}$R$_{20}$)$_{m''}$NR$_{13}$R$_{14}$;

m is 0, or the integer 1 or 2;

m' is an integer having a value of 1 or 2, m" is 0, or an integer having a value of 1 to 5;

n is 0, or an integer having a value of 1 to 10;

v is 0, or an integer having a value of 1 or 2;

$R_2$ is hydrogen, $(CR_{10}R_{23})_n$ $OR_9$, $(CR_{10}R_{23})_n OR_{11}$, $C_{1-10}$alkyl, halo-substituted $C_{1-10}$ alkyl, $C_{2-10}$ alkenyl, $C_{2-10}$ alkynyl, $C_{3-7}$ cycloalkyl, $C_{3-7}$ cycloalkyl$C_{1-10}$ alkyl, $C_{5-7}$ cycloalkenyl, $C_{5-7}$ cycloalkenyl $C_{1-10}$alkyl, aryl, aryl$C_{1-10}$ alkyl, heteroaryl, heteroaryl$C_{1-10}$alkyl, heterocyclyl, heterocyclyl$C_{1-10}$ alkyl, $(CR_{10}R_{23})_n S(O)_m$ $R_{18}$, $(CR_{10}R_{23})_n NHS(O)_2 R_{18}$, $(CR_{10}R_{23})_n NR_{13}R_{14}$, $(CR_{10}R_{23})_n NO_2$, $(CR_{10}R_{23})_n CN$, $(CR_{10}R_{23})_n S(O)_m NR_{13}R_{14}$, $(CR_{10}R_{230})_n C(Z)R_{11}$, $(CR_{10}R_{23})_n OC(Z)R_{11}$, $(CR_{10}R_{23})_n C(Z)OR_{11}$, $(CR_{10}R_{23})_n C(Z)NR_{13}R_{14}$, $(CR_{10}R_{23})_n C(Z)NR_{11}OR_9$, $(CR_{10}R_{23})_n NR_{10}C(Z)R_{11}$, $(CR_{10}R_{23})_n NR_{10}C(Z)NR_{13}R_{14}$, $(CR_{10}R_{23})_n N(OR_6)C(Z)NR_{13}R_{14}$, $(CR_{10}R_{23})_n N(OR_6)C(Z)R_{11}$, $(CR_{10}R_{23})_n C(=NOR_6)R_{11}$, $(CR_{10}R_{23})_n NR_{10}C(=NR_{19})NR_{13}R_{14}$, $(CR_{10}R_{23})_n OC(Z)NR_{13}R_{14}$, $(CR_{10}OR_{23})_n NR_{10}C(Z)NR_{13}R_{14}$, $(CR_{10}R_{23})_n NR_{10}C(Z)OR_{10}$, 5-($R_{18}$)-1,2,4-oxadizaol-3-yl or 4-($R_{12}$)-5-($R_{18}R_{19}$)-4,5-dihydro-1,2,4-oxadiazol-3-yl; wherein the cycloalkyl, cycloalkyl alkyl, aryl, arylalkyl, heteroaryl, heteroarylalkyl, heterocyclic and heterocyclic alkyl groups may be optionally substituted;

$R^3$ is heterocyclyl, heterocyclyl$C_{1-10}$ alkyl or $R_8$;

$R_5$ is hydrogen, $C_{1-4}$ alkyl, $C_{2-4}$ alkenyl, $C_{2-4}$ alkynyl or $NR_7R_{17}$, excluding the moieties $SR_5$ being $SNR_7R_{17}$ and $SOR_5$ being —SOH;

$R_6$ is hydrogen, a pharmaceutically acceptable cation, $C_{1-10}$ alkyl, $C_{3-7}$ cycloalkyl, aryl, aryl$C_{1-4}$ alkyl, heteroaryl, heteroaryl$C_{1-4}$ alkyl, heterocyclic, aroyl, or $C_{1-10}$ alkanoyl;

$R_7$ and $R_{17}$ is each independently selected from hydrogen or $C_{1-4}$ alkyl or $R_7$ and $R_{17}$ together with the nitrogen to which they are attached form a heterocyclic ring of 5 to 7 members which ring optionally contains an additional heteroatom selected from oxygen, sulfur or $NR_{15}$;

$R_8$ is $C_{1-10}$ alkyl, halo-substituted $C_{1-10}$ alkyl, $C_{2-10}$ alkenyl, $C_{2-10}$ alkynyl, $C_{3-7}$ cycloalkyl, $C_{5-7}$ cycloalkenyl, aryl, aryl$C_{1-10}$ alkyl, heteroaryl, heteroaryl$C_{1-10}$ alkyl, $(CR_{10}R_{20})_n OR_{11}$, $(CR_{10}R_{20})_n S(O)_m R_{18}$, $(CR_{10}R_{20})_n NHS(O)_2 R_{18}$, $(CR_{10}R_{20})_n NR_{13}R_{14}$; wherein the aryl, arylalkyl, heteroaryl, heteroaryl alkyl may be optionally substituted;

$R_9$ is hydrogen, $C(Z)R_{11}$ or optionally substituted $C_{1-10}$ alkyl, $S(O)_2R_{18}$, optionally substituted aryl or optionally substituted aryl-$C_{1-4}$ alkyl;

$R_{10}$ and $R_{20}$ is each independently selected from hydrogen or $C_{1-4}$ alkyl;

$R_{11}$ is hydrogen, $C_{1-10}$ alkyl, $C_{3-7}$ cycloalkyl, heterocyclyl, heterocyclyl $C_{1-10}$alkyl, aryl, aryl$C_{1-10}$ alkyl, heteroaryl or heteroaryl$C_{1-10}$ alkyl, wherein the aryl, arylalkyl, heteroaryl, heteroaryl alkyl, heterocyclyl or heterocyclylalkyl, may be optionally substituted;

$R_{12}$ is hydrogen or $R_{16}$;

$R_{13}$ and $R_{14}$ is each independently selected from hydrogen or optionally substituted $C_{1-4}$ alkyl, optionally substituted aryl or optionally substituted aryl-$C_{1-4}$ alkyl, or together with the nitrogen which they are attached form a heterocyclic ring of 5 to 7 members which ring optionally contains an additional heteroatom selected from oxygen, sulfur or $NR_9$;

$R_{15}$ is hydrogen, $C_{1-4}$ alkyl or $C(Z)$—$C_{1-4}$ alkyl;

$R_{16}$ is $C_{1-4}$ alkyl, halo-substituted-$C_{1-4}$ alkyl, or $C_{3-7}$ cycloalkyl;

$R_{18}$ is $C_{1-10}$ alkyl, $C_{3-7}$ cycloalkyl, heterocyclyl, aryl, aryl$C_{1-10}$ alkyl, heterocyclyl, heterocyclyl-$C_{1-10}$alkyl, heteroaryl or heteroarylalkyl, wherein the aryl, arylalkyl, heteroaryl, heteroaryl alkyl, heterocyclyl or heterocyclylalkyl may be optionally substituted;

$R_{19}$ is hydrogen, cyano, $C_{1-4}$ alkyl, $C_{3-7}$ cycloalkyl or aryl;

$R_{23}$ is hydrogen, $C_{1-6}$ alkyl, $C_{3-7}$ cycloalkyl, aryl, aryl$C_{1-4}$ alkyl, heteroaryl, heteroaryl$C_{1-4}$alkyl, heterocyclyl, or heterocyclyl$C_{1-4}$ alkyl moiety, all of which may be optionally substituted;

Z is oxygen or sulfur;

or a pharmaceutically acceptable salt thereof.

2. The compound according to claim 1 wherein $R_1$ is a substituted 4-pyrimidinyl.

3. The compound according to claim wherein the substituent is Y or NHR$_a$.

4. The compound according to claim 2 wherein $R_4$ is an optionally substituted phenyl.

5. The compound according to claim 4 wherein the phenyl is substituted one or more times independently by halogen, $SR_5$, $S(O)R_5$, $OR_{12}$, halo-substituted-$C_{1-4}$ alkyl, or $C_{1-4}$ alkyl.

6. The compound according to claim 1 wherein $R_2$ is selected from optionally substituted $C_4$ to $C_6$ cycloalkyl, optionally substituted $C_4$ or $C_6$ cycloalkyl $C_{1-4}$ alkyl, optionally substituted heterocyclic, optionally substituted heterocyclic $C_{1-4}$ alkyl, optionally substituted aryl, or optionally substituted aryl $C_{1-4}$ alkyl.

7. A pharmaceutical composition comprising a compound according to claim 1 a pharmaceutically acceptable carrier or diluent.

8. A method of treating the inflammatory component of a CSBP/RK/p38 kinase mediated disease, in a mammal in need thereof, which comprises administering to said mammal an effective amount of a compound of Formula (I) according to claim 1.

9. The method according to claim 8 wherein the CSBP/RK/p38 kinase mediated disease is psoriatic arthritis, Reiter's syndrome, rheumatoid arthritis, gout, traumatic arthritis, rubella arthritis and acute synovitis, rheumatoid spondylitis, osteoarthritis, gouty arthritis and other arthritic condition, sepsis, septic shock, endotoxic shock, gram negative sepsis, toxic shock syndrome, Alzheimer's disease, stroke, neurotrauma, asthma, adult respiratory distress syndrome, cerebral malaria, chronic pulmonary inflammatory disease, silicosis, pulmonary sarcososis, bone resorption disease, osteoporosis, restenosis, cardiac and renal reperfusion injury, chronic renal failure, congestive heart failure, angiogenic diseases, cancer, thrombosis, glomerularnephritis, diabetes, graft vs. host reaction, allograft rejection, inflammatory bowel disease, Crohn's disease, ulcerative colitis, multiple sclerosis, muscle degeneration, diabetic retinopathy, macular degeneration, tumor growth and metastasis, eczema, contact dermatitis, psoriasis, sunburn, or conjunctivitis.

10. A process for producing a compound of Formula:

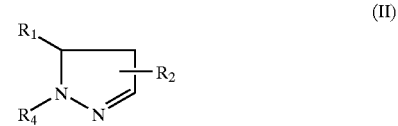

(II)

wherein $R_1$ is a 4-pyrimidinyl , 4-pyridazinyl, 4-triazin-5-yl, ring, which ring is optionally substituted independently independently one to three times with Y, NHR$_a$, optionally substituted C$_{1-4}$ alkyl, halogen, hydroxyl, optionally substituted C$_{1-4}$ alkoxy, optionally substituted C$_{1-4}$ alkylthio, optionally substituted C$_{1-4}$ alkylsulfinyl, CH$_2$OR$_{12}$, amino, mono and di-C$_{1-6}$ alkyl substituted amino, N(R$_{10}$)C(O)R$_b$; N(R$_{10}$)S(O)$_2$R$_d$ or an N-heterocyclyl ring which ring has from 5 to 7 members and optionally contains an additional heteroatom selected from oxygen, sulfur or NR$_{15}$;

Y is X$_1$—R$_a$;

X$_1$ is sulfur or oxygen;

R$_a$ is C$_{1-6}$alkyl, aryl, arylC$_{1-6}$alkyl, heterocyclic, heterocyclylC$_{1-6}$ alkyl, heteroaryl, or heteroarylC$_{1-6}$ alkyl, wherein each of these moieties may be optionally substituted;

R$_b$ is hydrogen, C$_{1-6}$ alkyl, C$_{3-7}$ cycloalkyl, aryl, arylC$_{1-4}$ alkyl, heteroaryl, heteroarylC$_{1-4}$alkyl, heterocyclyl, or heterocyclylC$_{1-4}$ alkyl;

R$_d$ is C$_{1-6}$ alkyl, C$_{3-7}$ cycloalkyl, aryl, arylC$_{1-4}$ alkyl, heteroaryl, heteroarylC$_{1-4}$alkyl, heterocyclyl, or heterocyclylC$_{1-4}$ alkyl;

R$_4$ is phenyl, naphth-1-yl or naphth-2-yl, or a fused phenyl containing ring system, which is optionally substituted by one to three substituents, each of which is independently selected, and which, for a 4-phenyl, 4-naphth-1-yl, 5-naphth-2-yl or 6-naphth-2-yl substituent, is halogen, cyano, nitro, C(Z)NR$_7$R$_{17}$, C(Z)OR$_{16}$, (CR$_{10}$R$_{20}$)$_v$COR$_{12}$, SR$_5$, SOR$_5$, OR$_{12}$, halo-substituted-C$_{1-4}$ alkyl, C$_{1-4}$ alkyl, ZC(Z)R$_{12}$, NR$_{10}$C(Z)R$_{16}$, or (CR$_{10}$R$_{20}$)$_v$NR$_{10}$R$_{20}$ and which, for other positions of substitution, is halogen, cyano, nitro, phenyl, C(Z)NR$_{13}$R$_{14}$, C(Z)OR$_3$, (CR$_{10}$R$_{20}$)$_{m''}$COR$_3$, S(O)$_m$R$_3$, OR$_3$, halo-substituted-C$_{1-4}$ alkyl, C$_{1-4}$ alkyl, (CR$_{10}$R$_{20}$)$_{m''}$NR$_{10}$C(Z)R$_3$, NR$_{10}$S(O)$_{m'}$R$_8$, NR$_{10}$S(O)$_{m'}$NR$_7$R$_{17}$, ZC(Z)R$_3$ or (CR$_{10}$R$_{20}$)$_{m''}$NR$_{13}$R$_{14}$;

n is 0, or an integer having a value of 1 to 10;

v is 0, or an integer having a value of 1 or 2;

m is 0, or the integer 1 or 2;

m' is an integer having a value of 1 or 2, m'' is 0, or an integer having a value of 1 to 5;

Z is oxygen or sulfur;

R$_2$ is hydrogen, (CR$_{10}$R$_{23}$)$_n$OR$_9$, (CR$_{10}$R$_{23}$)$_n$OR$_{11}$, C$_{1-10}$alkyl, halo-substituted C$_{1-10}$ alkyl, C$_{2-10}$ alkenyl, C$_{2-10}$ alkynyl, C$_{3-7}$ cycloalkyl, C$_{3-7}$ cycloalkylC$_{1-10}$ alkyl, C$_{5-7}$ cycloalkenyl, C$_{5-7}$ cycloalkenyl C$_{1-10}$alkyl, aryl, arylC$_{1-10}$ alkyl, heteroaryl, heteroarylC$_{1-10}$ alkyl, heterocyclyl, heterocyclylC$_{1-10}$ alkyl, (CR$_{10}$R$_{23}$)$_n$S(O)$_m$ R$_{18}$, (CR$_{10}$R$_{23}$)$_n$NHS(O)$_2$R$_{18}$, (CR$_{10}$R$_{23}$)$_n$NR$_{13}$R$_{14}$, (CR$_{10}$R$_{23}$)$_n$NO$_2$, (CR$_{10}$R$_{23}$)$_n$CN, (CR$_{10}$R$_{23}$)$_n$ S(O)$_m$NR$_{13}$R$_{14}$, (CR$_{10}$R$_{230}$)$_n$C(Z)R$_{11}$, (CR$_{10}$R$_{23}$)$_n$OC(Z)R$_{11}$, (CR$_{10}$R$_{23}$)$_n$C(Z)OR$_{11}$, (CR$_{10}$R$_{23}$)$_n$C(Z)NR$_{13}$R$_{14}$, (CR$_{10}$R$_{23}$)$_n$C(Z)NR$_{11}$OR$_9$, (CR$_{10}$R$_{23}$)$_n$NR$_{10}$C(Z)R$_{11}$, (CR$_{10}$R$_{23}$)$_n$NR$_{10}$C(Z)NR$_{13}$R$_{14}$, (CR$_{10}$R$_{23}$)$_n$N(OR$_6$)C(Z)NR$_{13}$R$_{14}$, (CR$_{10}$R$_{23}$)$_n$N(OR$_6$)C(Z)R$_{11}$, (CR$_{10}$R$_{23}$)$_n$C(=NOR$_6$)R$_{11}$, (CR$_{10}$R$_{23}$)$_n$NR$_{10}$C(=NR$_{19}$)NR$_{13}$R$_{14}$, (CR$_{10}$R$_{23}$)$_n$OC(Z)NR$_{13}$R$_{14}$, (CR$_{10}$R$_{23}$)$_n$NR$_{10}$C(Z)NR$_{13}$R$_{14}$, (CR$_{10}$R$_{23}$)$_n$NR$_{10}$ C(Z)OR$_{10}$, 5-(R$_{18}$)-1,2,4-oxadizaol-3-yl or 4-(R$_{12}$)-5-(R$_{18}$R$_{19}$)-4,5-dihydro-1,2,4-oxadiazol-3-yl; wherein the cycloalkyl, cycloalkyl alkyl, aryl, arylalkyl, heteroaryl, heteroaryl alkyl, heterocyclic and heterocyclic alkyl groups may be optionally substituted;

R$_3$ is heterocyclyl, heterocyclylC$_{1-10}$ alkyl or R$_8$;

R$_5$ is hydrogen, C$_{1-4}$ alkyl, C$_{2-4}$ alkenyl, C$_{2-4}$ alkynyl or NR$_7$R$_{17}$, excluding the moieties SR$_5$ being SNR$_7$R$_{17}$ and SOR$_5$ being SOH;

R$_6$ is hydrogen, a pharmaceutically acceptable cation, C$_{1-10}$ alkyl, C$_{3-7}$ cycloalkyl, aryl, arylC$_{1-4}$ alkyl, heteroaryl, heteroarylC$_{1-4}$ alkyl, heterocyclic, aroyl, or C$_{1-10}$ alkanoyl;

R$_7$ and R$_{17}$ is each independently selected from hydrogen or C$_{1-4}$ alkyl or R$_7$ and R$_{17}$ together with the nitrogen to which they are attached form a heterocyclic ring of 5 to 7 members which ring optionally contains an additional heteroatom selected from oxygen, sulfur or NR$_{15}$;

R$_8$ is C$_{1-10}$ alkyl, halo-substituted C$_{1-10}$ alkyl, C$_{2-10}$ alkenyl, C$_{2-10}$ alkynyl, C$_{3-7}$ cycloalkyl, C$_{5-7}$ cycloalkenyl, aryl, arylC$_{1-10}$ alkyl, heteroaryl, heteroarylC$_{1-10}$ alkyl, (CR$_{10}$R$_{20}$)$_n$OR$_{11}$, (CR$_{10}$R$_{20}$)$_n$S(O)$_m$R$_{18}$, (CR$_{10}$R$_{20}$)$_n$NHS(O)$_2$R$_{18}$, (CR$_{10}$R$_{20}$)$_n$NR$_{13}$R$_{14}$; wherein the aryl, arylalkyl, heteroaryl, heteroaryl alkyl may be optionally substituted;

R$_9$ is hydrogen, —C(Z)R$_{11}$ or optionally substituted C$_{1-10}$ alkyl, S(O)$_2$R$_{18}$, optionally substituted aryl or optionally substituted aryl-C$_{1-4}$ alkyl;

R$_{10}$ and R$_{20}$ is each independently selected from hydrogen or C$_{1-4}$ alkyl;

R$_{11}$ is hydrogen, C$_{1-10}$ alkyl, C$_{3-7}$ cycloalkyl, heterocyclyl, heterocyclyl C$_{1-10}$alkyl, aryl, arylC$_{1-10}$ alkyl, heteroaryl or heteroarylC$_{1-10}$ alkyl;

R$_{12}$ is hydrogen or R$_{16}$;

R$_{13}$ and R$_{14}$ is each independently selected from hydrogen or optionally substituted C$_{1-4}$ alkyl, optionally substituted aryl or optionally substituted aryl-C$_{1-4}$ alkyl, or together with the nitrogen which they are attached form a heterocyclic ring of 5 to 7 members which ring optionally contains an additional heteroatom selected from oxygen, sulfur or NR$_9$;

R$_{15}$ is hydrogen, C$_{1-4}$ alkyl or C(Z)—C$_{1-4}$ alkyl;

R$_{16}$ is C$_{1-4}$ alkyl, halo-substituted-C$_{1-4}$ alkyl, or C$_{3-7}$ cycloalkyl;

R$_{18}$ is C$_{1-10}$ alkyl, C$_{3-7}$ cycloalkyl, heterocyclyl, aryl, arylC$_{1-10}$ alkyl, heterocyclyl, heterocyclyl-C$_{1-10}$alkyl, heteroaryl or heteroarylalkyl;

R$_{19}$ is hydrogen, cyano, C$_{1-4}$ alkyl, C$_{3-7}$ cycloalkyl or aryl;

R$_{23}$ is hydrogen, C$_{1-6}$ alkyl, C$_{3-7}$ cycloalkyl, aryl, arylC$_{1-4}$ alkyl, heteroaryl, heteroarylC$_{1-4}$alkyl, heterocyclyl, or heterocyclylC$_{1-4}$ alkyl moiety, all of which may be optionally substituted;

or a pharmaceutically acceptable salt thereof.

11. The compound according to claim 10 wherein R$_1$ is a substituted 4-pyrimidinyl.

12. The compound according to claim 11 wherein the substituent is Y, or NHR$_a$.

13. The compound according to claim 11 R$_4$ is an optionally substituted phenyl.

14. The compound according to claim 13 wherein the phenyl is substituted one or more times independently by halogen, —SR$_5$, S(O)R$_5$, OR$_{12}$, halo-substituted-C$_{14}$ alkyl, or C$_{1-4}$ alkyl.

15. The compound according to claim 10 wherein R$_2$ is selected from optionally substituted C$_4$ to C$_6$cycloalkyl, optionally substituted C$_4$ or C$_6$ cycloalkylC$_{1-4}$ alkyl, optionally substituted heterocyclic, optionally substituted heterocyclicalkyl, optionally substituted aryl, or optionally substituted aryl alkyl.

16. A pharmaceutical composition comprising a compound according to claim 10 and a pharmaceutically acceptable carrier or diluent.

17. A method of treating the inflammatory component of a CSBP/RK/p38 kinase mediated disease, in a mammal in need thereof, which comprises administering to said mammal an effective amount of a compound of Formula (II) according to claim 10.

18. The method according to claim 17 wherein the CSBP/RK/p38 kinase mediated disease is psoriatic arthritis, Reiter's syndrome, rheumatoid arthritis, gout, traumatic arthritis, rubella arthritis and acute synovitis, rheumatoid spondylitis, osteoarthritis, gouty arthritis and other arthritic condition, sepsis, septic shock, endotoxic shock, gram negative sepsis, toxic shock syndrome, Alzheimer's disease, stroke, neurotrauma, asthma, adult respiratory distress syndrome, cerebral malaria, chronic pulmonary inflammatory disease, silicosis, pulmonary sarcososis, bone resorption disease, osteoporosis, restenosis, cardiac and renal reperfusion injury, chronic renal failure, congestive heart failure, angiogenic diseases, cancer, thrombosis, glomerularnephritis, diabetes, graft vs. host reaction, allograft rejection, inflammatory bowel disease, Crohn's disease, ulcerative colitis, multiple sclerosis, muscle degeneration, diabetic retinopathy, macular degeneration, tumor growth and metastasis, eczema, contact dermatitis, psoriasis, sunburn, or conjunctivitis.

19. A process for producing a compound of Formula (I), according to claim 1 wherein $R_1$ is an optionally substituted pyrimidinyl, which process comprises cyclizing a compound of the formula:

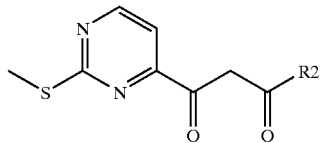

wherein $R_2$ is an optionally substituted phenyl, as defined according to formula (I); with a compound of the formula: $R_4NHNH_2$, wherein $R_4$ is as defined for Formula (I), to yield a compound of Formula (I), or if necessary, converting a precursor of $R_1$, $R_2$ and $R_4$ to a group $R_1$, $R_2$ and $R_4$.

* * * * *